(12) United States Patent
Wales et al.

(10) Patent No.: US 8,460,319 B2
(45) Date of Patent: Jun. 11, 2013

(54) INTERVERTEBRAL DISC ANNULUS REPAIR SYSTEM AND METHOD

(75) Inventors: Lawrence W. Wales, Maplewood, MN (US); Ishmael Bentley, Eagan, MN (US); Emily Daley, Coon Rapids, MN (US); Michael Lancial, St. Louis Park, MN (US)

(73) Assignee: Anulex Technologies, Inc., Minnetonka, MN (US)

( * ) Notice: Subject to any disclaimer, the term of this patent is extended or adjusted under 35 U.S.C. 154(b) by 339 days.

(21) Appl. No.: 12/853,843

(22) Filed: Aug. 10, 2010

(65) Prior Publication Data

US 2011/0172701 A1 Jul. 14, 2011

Related U.S. Application Data

(60) Provisional application No. 61/293,939, filed on Jan. 11, 2010, provisional application No. 61/323,679, filed on Apr. 13, 2010.

(51) Int. Cl.
*A61B 17/04* (2006.01)

(52) U.S. Cl.
USPC ............................ 606/144; 606/151; 606/212

(58) Field of Classification Search
USPC ......... 606/86 R, 144, 151, 213, 232; 128/898
See application file for complete search history.

(56) References Cited

U.S. PATENT DOCUMENTS

| | | |
|---|---|---|
| 3,875,595 A | 4/1975 | Froning |
| 3,895,753 A | 7/1975 | Bone |
| 3,990,619 A | 11/1976 | Russell |
| 4,006,747 A | 2/1977 | Kronenthal et al. |
| 4,007,743 A | 2/1977 | Blake |
| 4,013,078 A | 3/1977 | Field |
| 4,059,115 A | 11/1977 | Jamushev |
| 4,224,413 A | 9/1980 | Burbidge |
| 4,502,161 A | 3/1985 | Wall |
| 4,512,338 A | 4/1985 | Balko et al. |

(Continued)

FOREIGN PATENT DOCUMENTS

| | | |
|---|---|---|
| DE | 43 23 959501 | 7/1994 |
| EP | 0 020 021 | 12/1980 |

(Continued)

OTHER PUBLICATIONS

International Search Report and Written Opinion issued in PCT/US2011/020699, mailed Jul. 26, 2011, 24 pages.

(Continued)

*Primary Examiner* — Vy Q Bui
(74) *Attorney, Agent, or Firm* — Faegre Baker Daniels LLP

(57) ABSTRACT

A device for at least partially closing an aperture in an annulus fibrosus of an intervertebral disc of a patient comprises an implant delivery tool and an implant releasably coupled to the implant delivery tool. The implant delivery tool includes a substantially rigid outer tube having a sharpened distal tip, a body a body coupled to the proximal section of the outer tube, and a plunger assembly axially movable relative to the body and including a plunger member and a pusher tube coupled thereto and disposed within the outer tube. The implant includes first and second tissue anchors serially disposed within the distal section of the outer tube, and a flexible connecting element coupling the first and second tissue anchors including a knotless braided suture structure for adjusting the length of the flexible coupling element.

25 Claims, 22 Drawing Sheets

U.S. PATENT DOCUMENTS

| | | |
|---|---|---|
| 4,532,926 A | 8/1985 | O'Holla |
| 4,545,374 A | 10/1985 | Jacobson |
| 4,602,635 A | 7/1986 | Mulhollan et al. |
| 4,632,100 A | 12/1986 | Somers et al. |
| 4,662,886 A | 5/1987 | Moorse |
| 4,663,358 A | 5/1987 | Hyon et al. |
| 4,669,473 A | 6/1987 | Richards et al. |
| 4,678,459 A | 7/1987 | Onik et al. |
| 4,731,084 A | 3/1988 | Dunn et al. |
| 4,736,746 A | 4/1988 | Anderson |
| 4,741,330 A | 5/1988 | Hayhurst |
| 4,743,260 A | 5/1988 | Burton |
| 4,744,364 A | 5/1988 | Kensey |
| 4,772,287 A | 9/1988 | Ray et al. |
| 4,781,190 A | 11/1988 | Lee |
| 4,790,850 A | 12/1988 | Dunn et al. |
| 4,798,205 A | 1/1989 | Bonomo et al. |
| 4,834,757 A | 5/1989 | Brantigan |
| 4,837,285 A | 6/1989 | Berg et al. |
| 4,844,088 A | 7/1989 | Kambin |
| 4,852,568 A | 8/1989 | Kensey |
| 4,863,477 A | 9/1989 | Monson |
| 4,873,976 A | 10/1989 | Schreiber |
| 4,884,572 A | 12/1989 | Bays et al. |
| 4,890,612 A | 1/1990 | Kensey |
| 4,895,148 A | 1/1990 | Bays et al. |
| 4,904,260 A | 2/1990 | Ray et al. |
| 4,904,261 A | 2/1990 | Dove et al. |
| 4,911,718 A | 3/1990 | Lee et al. |
| 4,917,704 A | 4/1990 | Frey et al. |
| 4,919,667 A | 4/1990 | Richmond |
| 4,932,969 A | 6/1990 | Frey et al. |
| 4,946,377 A | 8/1990 | Kovach |
| 4,946,378 A | 8/1990 | Hirayama et al. |
| 4,955,908 A | 9/1990 | Frey et al. |
| 4,959,069 A | 9/1990 | Brennan et al. |
| 4,976,715 A | 12/1990 | Bays et al. |
| 5,002,576 A | 3/1991 | Fuhrmann et al. |
| 5,015,255 A | 5/1991 | Kuslich |
| 5,021,059 A | 6/1991 | Kensey et al. |
| 5,035,716 A | 7/1991 | Downey |
| 5,041,129 A | 8/1991 | Hayhurst et al. |
| 5,047,055 A | 9/1991 | Bao |
| 5,053,046 A | 10/1991 | Janese |
| 5,059,193 A | 10/1991 | Kuslich |
| 5,059,206 A | 10/1991 | Winters |
| 5,061,274 A | 10/1991 | Kensey |
| 5,062,344 A | 11/1991 | Gerker |
| 5,071,437 A | 12/1991 | Steffee |
| 5,085,661 A | 2/1992 | Moss |
| 5,100,422 A | 3/1992 | Berguer et al. |
| 5,108,420 A | 4/1992 | Marks |
| 5,108,438 A | 4/1992 | Stone |
| 5,116,357 A | 5/1992 | Eberbach |
| 5,122,154 A | 6/1992 | Rhodes |
| 5,122,155 A | 6/1992 | Eberbach |
| 5,123,913 A | 6/1992 | Wilk et al. |
| 5,123,926 A | 6/1992 | Pisharodi |
| 5,129,912 A | 7/1992 | Noda et al. |
| 5,141,515 A | 8/1992 | Eberbach |
| 5,147,374 A | 9/1992 | Fernandez |
| 5,171,259 A | 12/1992 | Inoue |
| 5,171,278 A | 12/1992 | Pisharodi |
| 5,171,280 A | 12/1992 | Baumgartner |
| 5,171,281 A | 12/1992 | Parsons et al. |
| 5,176,682 A | 1/1993 | Chow |
| 5,176,691 A | 1/1993 | Pierce |
| 5,176,692 A | 1/1993 | Wilk et al. |
| 5,192,326 A | 3/1993 | Bao et al. |
| 5,195,541 A | 3/1993 | Obenchain |
| 5,203,787 A | 4/1993 | Noblitt et al. |
| 5,204,106 A | 4/1993 | Schepers et al. |
| 5,207,695 A | 5/1993 | Trout |
| 5,211,650 A | 5/1993 | Noda |
| 5,222,962 A | 6/1993 | Burkhart |
| 5,222,974 A | 6/1993 | Kensey et al. |
| 5,224,946 A | 7/1993 | Hayhurst et al. |
| 5,242,439 A | 9/1993 | Larsen et al. |
| 5,254,133 A | 10/1993 | Seid |
| 5,258,000 A | 11/1993 | Gianturco |
| 5,258,043 A | 11/1993 | Stone |
| 5,269,783 A | 12/1993 | Sander |
| 5,269,791 A | 12/1993 | Mayzels et al. |
| 5,269,809 A | 12/1993 | Hayhurst et al. |
| 5,282,827 A | 2/1994 | Kensey et al. |
| 5,282,863 A | 2/1994 | Burton |
| 5,304,194 A | 4/1994 | Chee et al. |
| 5,306,311 A | 4/1994 | Stone et al. |
| 5,312,435 A | 5/1994 | Nash et al. |
| 5,313,962 A | 5/1994 | Obenchain |
| 5,318,575 A | 6/1994 | Chesterfield et al. |
| 5,320,629 A | 6/1994 | Noda et al. |
| 5,320,633 A | 6/1994 | Allen et al. |
| 5,320,644 A | 6/1994 | Baumgartner |
| 5,342,393 A | 8/1994 | Stack |
| 5,342,394 A | 8/1994 | Matsuno et al. |
| 5,344,442 A | 9/1994 | Deac |
| 5,354,736 A | 10/1994 | Bhatnagar |
| 5,356,432 A | 10/1994 | Rutkow et al. |
| 5,366,460 A | 11/1994 | Eberbach |
| 5,368,602 A | 11/1994 | de la Torre |
| 5,370,660 A | 12/1994 | Weinstein et al. |
| 5,370,662 A | 12/1994 | Stone et al. |
| 5,370,697 A | 12/1994 | Baumgartner |
| 5,374,268 A | 12/1994 | Sander |
| 5,376,120 A | 12/1994 | Sarver et al. |
| 5,383,477 A | 1/1995 | DeMatteis |
| 5,383,905 A | 1/1995 | Golds et al. |
| 5,390,683 A | 2/1995 | Pisharodi |
| 5,391,182 A | 2/1995 | Chin |
| 5,397,326 A | 3/1995 | Mangum |
| 5,397,331 A | 3/1995 | Himpens et al. |
| 5,397,332 A | 3/1995 | Kammerer et al. |
| 5,397,991 A | 3/1995 | Rogers |
| 5,398,861 A | 3/1995 | Green |
| 5,405,352 A | 4/1995 | Weston |
| 5,405,359 A | 4/1995 | Pierce |
| 5,405,360 A | 4/1995 | Tovey |
| 5,411,523 A | 5/1995 | Goble |
| 5,417,691 A | 5/1995 | Hayhurst |
| 5,417,699 A | 5/1995 | Klein et al. |
| 5,425,772 A | 6/1995 | Brantigan |
| 5,425,773 A | 6/1995 | Boyd et al. |
| 5,429,598 A | 7/1995 | Waxman et al. |
| 5,437,631 A | 8/1995 | Janzen |
| 5,437,680 A | 8/1995 | Yoon |
| 5,439,464 A | 8/1995 | Shapiro |
| 5,441,502 A | 8/1995 | Bartlett |
| 5,456,720 A | 10/1995 | Schultz et al. |
| 5,464,407 A | 11/1995 | McGuire |
| 5,464,425 A | 11/1995 | Skiba |
| 5,464,426 A | 11/1995 | Bonutti |
| 5,470,337 A | 11/1995 | Moss |
| 5,489,307 A | 2/1996 | Kuslich et al. |
| 5,492,697 A | 2/1996 | Boyan et al. |
| 5,496,348 A | 3/1996 | Bonutti |
| 5,500,000 A | 3/1996 | Feagin et al. |
| 5,507,754 A | 4/1996 | Green et al. |
| 5,507,755 A | 4/1996 | Gresl et al. |
| 5,514,180 A | 5/1996 | Heggeness et al. |
| 5,520,696 A | 5/1996 | Wenstrom, Jr. |
| 5,520,700 A | 5/1996 | Beyar et al. |
| 5,527,342 A | 6/1996 | Pietrzak et al. |
| 5,527,343 A | 6/1996 | Bonutti |
| 5,531,678 A | 7/1996 | Tomba et al. |
| 5,531,759 A | 7/1996 | Kensey et al. |
| 5,534,012 A | 7/1996 | Bonutti |
| 5,534,028 A | 7/1996 | Bao et al. |
| 5,534,030 A | 7/1996 | Navarro et al. |
| 5,540,703 A | 7/1996 | Barker et al. |
| 5,540,704 A | 7/1996 | Gordon et al. |
| 5,540,715 A | 7/1996 | Katsaros et al. |
| 5,545,178 A | 8/1996 | Kensey et al. |
| 5,545,229 A | 8/1996 | Parsons et al. |
| 5,549,617 A | 8/1996 | Green et al. |
| 5,549,679 A | 8/1996 | Kuslich |
| 5,556,428 A | 9/1996 | Shah |

| Patent | Date | Inventor |
|---|---|---|
| 5,556,429 A | 9/1996 | Felt |
| 5,562,684 A | 10/1996 | Kammerer |
| 5,562,689 A | 10/1996 | Green et al. |
| 5,562,736 A | 10/1996 | Ray et al. |
| 5,562,738 A | 10/1996 | Boyd et al. |
| 5,569,242 A | 10/1996 | Lax et al. |
| 5,569,252 A | 10/1996 | Justin et al. |
| 5,569,303 A | 10/1996 | Johnson |
| 5,569,306 A | 10/1996 | Thal |
| 5,571,189 A | 11/1996 | Kuslich |
| 5,573,286 A | 11/1996 | Rogozinski |
| 5,573,548 A | 11/1996 | Nazre et al. |
| 5,578,057 A | 11/1996 | Wenstrom, Jr. |
| 5,582,616 A | 12/1996 | Bolduc et al. |
| 5,584,862 A | 12/1996 | Bonutti |
| 5,591,177 A | 1/1997 | Lehrer |
| 5,591,223 A | 1/1997 | Lock et al. |
| 5,593,425 A | 1/1997 | Bonutti et al. |
| 5,599,279 A | 2/1997 | Slotman et al. |
| 5,601,557 A | 2/1997 | Hayhurst |
| 5,601,571 A | 2/1997 | Moss |
| 5,613,974 A | 3/1997 | Andreas et al. |
| 5,618,314 A | 4/1997 | Harwin et al. |
| 5,620,012 A | 4/1997 | Benderev et al. |
| 5,624,463 A | 4/1997 | Stone et al. |
| 5,626,612 A | 5/1997 | Bartlett et al. |
| 5,626,613 A | 5/1997 | Schmieding |
| 5,626,614 A | 5/1997 | Hart |
| 5,628,756 A | 5/1997 | Barker et al. |
| 5,634,931 A | 6/1997 | Kugel |
| 5,634,944 A | 6/1997 | Magram |
| 5,643,319 A | 7/1997 | Green et al. |
| 5,643,320 A | 7/1997 | Lower et al. |
| 5,645,084 A | 7/1997 | McKay |
| 5,645,597 A | 7/1997 | Krapiva |
| 5,649,945 A | 7/1997 | Ray et al. |
| 5,658,343 A | 8/1997 | Hauselmann et al. |
| 5,662,658 A | 9/1997 | Wenstrom, Jr. |
| 5,662,681 A | 9/1997 | Nash et al. |
| 5,662,683 A | 9/1997 | Kay |
| 5,669,935 A | 9/1997 | Rosenman et al. |
| 5,674,294 A | 10/1997 | Bainville et al. |
| 5,674,296 A | 10/1997 | Bryan et al. |
| 5,676,698 A | 10/1997 | Janzen et al. |
| 5,676,701 A | 10/1997 | Yuan et al. |
| 5,681,310 A | 10/1997 | Yuan et al. |
| 5,681,351 A | 10/1997 | Jamiolkowski et al. |
| 5,683,417 A | 11/1997 | Cooper |
| 5,683,418 A | 11/1997 | Luscombe et al. |
| 5,683,419 A | 11/1997 | Thal |
| 5,683,465 A | 11/1997 | Shinn et al. |
| 5,690,677 A | 11/1997 | Schmieding et al. |
| 5,695,525 A | 12/1997 | Mulhauser et al. |
| 5,697,950 A | 12/1997 | Fucci et al. |
| 5,699,657 A | 12/1997 | Paulson |
| 5,702,449 A | 12/1997 | McKay |
| 5,702,450 A | 12/1997 | Bisserie |
| 5,702,451 A | 12/1997 | Biedermann et al. |
| 5,702,454 A | 12/1997 | Baumgartner |
| 5,702,462 A | 12/1997 | Oberlander |
| 5,704,943 A | 1/1998 | Yoon et al. |
| 5,709,708 A | 1/1998 | Thal |
| 5,716,404 A | 2/1998 | Vacanti et al. |
| 5,716,408 A | 2/1998 | Eldridge et al. |
| 5,716,409 A | 2/1998 | Debbas |
| 5,716,413 A | 2/1998 | Walter et al. |
| 5,716,416 A | 2/1998 | Lin |
| 5,718,717 A | 2/1998 | Bonutti |
| 5,725,552 A | 3/1998 | Kotula et al. |
| 5,725,577 A | 3/1998 | Saxon |
| 5,728,109 A | 3/1998 | Schulze et al. |
| 5,728,150 A | 3/1998 | McDonald et al. |
| 5,730,744 A | 3/1998 | Justin et al. |
| 5,733,307 A | 3/1998 | Dinsdale |
| 5,733,337 A | 3/1998 | Carr, Jr. et al. |
| 5,735,875 A | 4/1998 | Bonutti |
| 5,736,746 A | 4/1998 | Furutoh |
| 5,743,917 A | 4/1998 | Saxon |
| 5,746,755 A | 5/1998 | Wood et al. |
| 5,752,964 A | 5/1998 | Mericle |
| 5,755,797 A | 5/1998 | Baumgartner |
| 5,759,189 A | 6/1998 | Ferragamo et al. |
| 5,766,246 A | 6/1998 | Mulhauser et al. |
| 5,769,864 A | 6/1998 | Kugel |
| 5,769,893 A | 6/1998 | Shah |
| 5,772,661 A | 6/1998 | Michelson |
| 5,776,183 A | 7/1998 | Kanesaka et al. |
| 5,782,844 A | 7/1998 | Yoon et al. |
| 5,782,860 A | 7/1998 | Epstein et al. |
| 5,782,864 A | 7/1998 | Lizardi |
| 5,785,705 A | 7/1998 | Baker |
| 5,786,217 A | 7/1998 | Tubo et al. |
| 5,788,625 A | 8/1998 | Plouhar et al. |
| 5,792,152 A | 8/1998 | Klein et al. |
| 5,797,929 A | 8/1998 | Andreas et al. |
| 5,800,549 A | 9/1998 | Bao et al. |
| 5,800,550 A | 9/1998 | Sertich |
| 5,810,848 A | 9/1998 | Hayhurst |
| 5,810,851 A | 9/1998 | Yoon |
| 5,814,051 A | 9/1998 | Wenstrom, Jr. |
| 5,823,994 A | 10/1998 | Sharkey et al. |
| 5,824,008 A | 10/1998 | Bolduc et al. |
| 5,824,011 A | 10/1998 | Stone et al. |
| 5,824,082 A | 10/1998 | Brown |
| 5,824,093 A | 10/1998 | Ray et al. |
| 5,824,094 A | 10/1998 | Serhan et al. |
| 5,827,298 A | 10/1998 | Hart et al. |
| 5,827,325 A | 10/1998 | Landgrebe et al. |
| 5,827,328 A | 10/1998 | Butterman |
| 5,836,315 A | 11/1998 | Benderev et al. |
| 5,842,477 A | 12/1998 | Naughton et al. |
| 5,843,084 A | 12/1998 | Hart et al. |
| 5,846,261 A | 12/1998 | Kotula et al. |
| 5,849,331 A | 12/1998 | Ducheyne et al. |
| 5,851,219 A | 12/1998 | Goble et al. |
| 5,853,422 A | 12/1998 | Huebsch et al. |
| 5,855,614 A | 1/1999 | Stevens et al. |
| 5,860,425 A | 1/1999 | Benderev et al. |
| 5,860,977 A | 1/1999 | Zucherman et al. |
| 5,865,845 A | 2/1999 | Thalgott |
| 5,865,846 A | 2/1999 | Bryan et al. |
| 5,868,762 A | 2/1999 | Cragg et al. |
| 5,879,366 A | 3/1999 | Shaw et al. |
| 5,888,220 A | 3/1999 | Felt et al. |
| 5,888,222 A | 3/1999 | Coates |
| 5,888,226 A | 3/1999 | Rogozinski |
| 5,891,146 A | 4/1999 | Simon et al. |
| 5,893,592 A | 4/1999 | Schulze et al. |
| 5,893,889 A | 4/1999 | Harrington |
| 5,895,426 A | 4/1999 | Scarborough et al. |
| 5,899,920 A | 5/1999 | DeSatnick et al. |
| 5,904,703 A | 5/1999 | Gilson |
| 5,916,225 A | 6/1999 | Kugel |
| 5,919,235 A | 7/1999 | Husson et al. |
| 5,922,026 A | 7/1999 | Chin |
| 5,922,028 A | 7/1999 | Plouhar et al. |
| 5,928,284 A | 7/1999 | Mehdizadeh |
| 5,935,147 A | 8/1999 | Kensey et al. |
| 5,941,439 A | 8/1999 | Kammerer et al. |
| 5,944,738 A | 8/1999 | Amplatz et al. |
| 5,948,001 A | 9/1999 | Larsen |
| 5,948,002 A | 9/1999 | Bonutti |
| 5,954,716 A | 9/1999 | Sharkey et al. |
| 5,954,767 A | 9/1999 | Pajotin et al. |
| 5,957,939 A | 9/1999 | Heaven et al. |
| 5,961,538 A | 10/1999 | Pedlick et al. |
| 5,961,539 A * | 10/1999 | Northrup et al. ............... 606/232 |
| 5,964,783 A | 10/1999 | Grafton et al. |
| 5,964,807 A | 10/1999 | Gan et al. |
| 5,970,697 A | 10/1999 | Jacobs et al. |
| 5,972,000 A | 10/1999 | Beyar et al. |
| 5,972,007 A | 10/1999 | Sheffield et al. |
| 5,972,022 A | 10/1999 | Huxel |
| 5,976,174 A | 11/1999 | Ruiz |
| 5,976,186 A | 11/1999 | Bao et al. |
| 5,980,504 A | 11/1999 | Sharkey et al. |
| 5,980,558 A | 11/1999 | Wiley |
| 5,984,948 A | 11/1999 | Hasson |

| | | | | | | |
|---|---|---|---|---|---|---|
| 6,001,130 | A | 12/1999 | Bryan et al. | 6,312,448 | B1 | 11/2001 | Bonutti |
| 6,007,567 | A | 12/1999 | Bonutti | 6,319,263 | B1 | 11/2001 | Levinson |
| 6,007,570 | A | 12/1999 | Sharkey et al. | 6,332,894 | B1 | 12/2001 | Stalcup |
| 6,007,575 | A | 12/1999 | Samuels | 6,340,369 | B1 | 1/2002 | Ferree |
| 6,010,525 | A | 1/2000 | Bonutti et al. | 6,342,064 | B1 | 1/2002 | Koike et al. |
| 6,019,792 | A | 2/2000 | Cauthen | 6,344,057 | B1 | 2/2002 | Rabbe et al. |
| 6,019,793 | A | 2/2000 | Perren et al. | 6,344,058 | B1 | 2/2002 | Ferree |
| 6,024,096 | A | 2/2000 | Buckberg | 6,352,557 | B1 | 3/2002 | Ferree |
| 6,024,754 | A | 2/2000 | Engelson | 6,355,052 | B1 | 3/2002 | Neuss |
| 6,024,758 | A | 2/2000 | Thal | 6,364,897 | B1 | 4/2002 | Bonutti |
| 6,027,523 | A | 2/2000 | Schmieding | 6,371,984 | B1 | 4/2002 | Van Dyke et al. |
| 6,027,527 | A | 2/2000 | Asano et al. | 6,371,990 | B1 | 4/2002 | Ferree |
| 6,036,699 | A | 3/2000 | Andreas et al. | 6,391,060 | B1 | 5/2002 | Ory et al. |
| 6,039,761 | A | 3/2000 | Li et al. | 6,402,750 | B1 | 6/2002 | Atkinson et al. |
| 6,039,762 | A | 3/2000 | McKay | 6,402,784 | B1 | 6/2002 | Wardlaw |
| 6,045,561 | A | 4/2000 | Marshall et al. | 6,402,785 | B1 | 6/2002 | Zdeblick |
| 6,045,573 | A | 4/2000 | Wenstrom, Jr. et al. | 6,409,739 | B1 | 6/2002 | Nobles et al. |
| 6,053,909 | A | 4/2000 | Shadduck | 6,419,676 | B1 | 7/2002 | Zucherman et al. |
| 6,063,378 | A | 5/2000 | Nohara et al. | 6,419,702 | B1 | 7/2002 | Ferree |
| 6,066,146 | A | 5/2000 | Carroll et al. | 6,419,703 | B1 | 7/2002 | Fallin et al. |
| 6,066,776 | A | 5/2000 | Goodwin et al. | 6,419,704 | B1 | 7/2002 | Ferree |
| 6,068,648 | A | 5/2000 | Cole et al. | 6,419,706 | B1 | 7/2002 | Graf |
| 6,073,051 | A | 6/2000 | Sharkey et al. | 6,423,065 | B2 | 7/2002 | Ferree |
| 6,080,182 | A | 6/2000 | Shaw et al. | 6,423,080 | B1 | 7/2002 | Gellman et al. |
| 6,093,205 | A | 7/2000 | McLeod et al. | 6,425,919 | B1 | 7/2002 | Lambrecht |
| 6,095,149 | A | 8/2000 | Sharkey et al. | 6,425,924 | B1 | 7/2002 | Rousseau |
| 6,099,514 | A | 8/2000 | Sharkey et al. | 6,428,562 | B2 | 8/2002 | Bonutti |
| 6,102,934 | A | 8/2000 | Li | 6,428,576 | B1 | 8/2002 | Haldimann |
| 6,106,545 | A | 8/2000 | Egan | 6,432,107 | B1 | 8/2002 | Ferree |
| 6,113,609 | A | 9/2000 | Adams | 6,432,123 | B2 | 8/2002 | Schwartz et al. |
| 6,113,623 | A | 9/2000 | Sgro | 6,436,098 | B1 | 8/2002 | Michelson |
| 6,113,639 | A | 9/2000 | Ray et al. | 6,436,099 | B1 | 8/2002 | Drewry et al. |
| 6,117,162 | A | 9/2000 | Schmieding et al. | 6,436,143 | B1 | 8/2002 | Ross et al. |
| 6,123,715 | A | 9/2000 | Amplatz | 6,443,988 | B2 | 9/2002 | Felt et al. |
| 6,126,682 | A | 10/2000 | Sharkey et al. | 6,447,531 | B1 | 9/2002 | Amplatz |
| 6,139,565 | A | 10/2000 | Stone et al. | 6,452,924 | B1 | 9/2002 | Golden et al. |
| 6,140,452 | A | 10/2000 | Felt et al. | 6,454,804 | B1 | 9/2002 | Ferree |
| 6,143,006 | A | 11/2000 | Chan et al. | 6,464,712 | B1 | 10/2002 | Epstein |
| 6,143,017 | A | 11/2000 | Thal | 6,482,235 | B1 | 11/2002 | Lambrecht et al. |
| 6,146,380 | A | 11/2000 | Racz et al. | 6,488,691 | B1 | 12/2002 | Carroll et al. |
| 6,146,406 | A | 11/2000 | Shluzas et al. | 6,491,724 | B1 | 12/2002 | Ferree |
| 6,146,422 | A | 11/2000 | Lawson | 6,494,883 | B1 | 12/2002 | Ferree |
| 6,162,203 | A | 12/2000 | Haago | 6,500,132 | B1 | 12/2002 | Li |
| 6,168,598 | B1 | 1/2001 | Martello | 6,500,184 | B1 | 12/2002 | Chan et al. |
| 6,171,317 | B1 | 1/2001 | Jackson et al. | 6,508,828 | B1 | 1/2003 | Akerfeldt et al. |
| 6,171,318 | B1 | 1/2001 | Kugel et al. | 6,508,839 | B1 | 1/2003 | Lambrecht et al. |
| 6,171,329 | B1 | 1/2001 | Shaw et al. | 6,511,488 | B1 | 1/2003 | Marshall et al. |
| 6,174,322 | B1 | 1/2001 | Schneidt | 6,511,498 | B1 | 1/2003 | Fumex |
| 6,176,863 | B1 | 1/2001 | Kugel et al. | 6,511,958 | B1 | 1/2003 | Atkinson et al. |
| 6,179,874 | B1 | 1/2001 | Cauthen | 6,514,255 | B1 | 2/2003 | Ferree |
| 6,179,879 | B1 | 1/2001 | Robinson et al. | 6,514,514 | B1 | 2/2003 | Atkinson et al. |
| 6,183,479 | B1 | 2/2001 | Tormala et al. | 6,524,317 | B1 | 2/2003 | Ritchart et al. |
| 6,183,518 | B1 | 2/2001 | Ross et al. | 6,527,794 | B1 | 3/2003 | McDevitt et al. |
| 6,187,048 | B1 | 2/2001 | Milner et al. | 6,527,795 | B1 | 3/2003 | Lizardi |
| 6,190,401 | B1 | 2/2001 | Green et al. | 6,530,933 | B1 | 3/2003 | Yeung et al. |
| 6,200,329 | B1 | 3/2001 | Fung et al. | 6,533,799 | B1 | 3/2003 | Bouchier |
| 6,203,554 | B1 | 3/2001 | Roberts | 6,533,817 | B1 | 3/2003 | Norton et al. |
| 6,203,565 | B1 | 3/2001 | Bonutti | 6,544,267 | B1 | 4/2003 | Cole et al. |
| 6,206,895 | B1 | 3/2001 | Levinson | 6,547,800 | B2 | 4/2003 | Foerster et al. |
| 6,206,921 | B1 | 3/2001 | Guagliano et al. | 6,547,806 | B1 | 4/2003 | Ding |
| 6,221,092 | B1 | 4/2001 | Koike et al. | 6,558,386 | B1 | 5/2003 | Cragg |
| 6,221,109 | B1 | 4/2001 | Geistlich et al. | 6,558,390 | B2 | 5/2003 | Cragg |
| 6,224,630 | B1 | 5/2001 | Bao et al. | 6,562,052 | B2 | 5/2003 | Nobles et al. |
| 6,228,096 | B1 | 5/2001 | Marchand | 6,569,187 | B1 | 5/2003 | Bonutti et al. |
| 6,231,615 | B1 | 5/2001 | Preissman | 6,569,442 | B2 | 5/2003 | Gan et al. |
| 6,241,768 | B1 | 6/2001 | Agarwal et al. | 6,572,635 | B1 | 6/2003 | Bonutti |
| 6,245,080 | B1 | 6/2001 | Levinson | 6,572,653 | B1 | 6/2003 | Simonson |
| 6,245,107 | B1 | 6/2001 | Ferree | 6,575,979 | B1 | 6/2003 | Cragg |
| 6,248,106 | B1 | 6/2001 | Ferree | 6,576,017 | B2 | 6/2003 | Foley et al. |
| 6,248,131 | B1 | 6/2001 | Felt et al. | 6,579,291 | B1 | 6/2003 | Keith et al. |
| 6,258,094 | B1 | 7/2001 | Nicholson et al. | 6,582,453 | B1 | 6/2003 | Tran et al. |
| 6,264,677 | B1 | 7/2001 | Simon et al. | 6,592,608 | B2 | 7/2003 | Fisher et al. |
| 6,267,772 | B1 | 7/2001 | Mulhauser et al. | 6,592,609 | B1 | 7/2003 | Bonutti |
| 6,280,453 | B1 | 8/2001 | Kugel et al. | 6,592,625 | B2 | 7/2003 | Cauthen |
| 6,287,324 | B1 | 9/2001 | Yarnitsky et al. | 6,596,012 | B2 | 7/2003 | Akerfeldt et al. |
| 6,293,961 | B2 | 9/2001 | Schwartz et al. | 6,602,291 | B1 | 8/2003 | Ray et al. |
| 6,296,659 | B1 | 10/2001 | Foerster | 6,605,096 | B1 | 8/2003 | Ritchart |
| 6,306,159 | B1 | 10/2001 | Schwartz et al. | 6,607,541 | B1 | 8/2003 | Gardiner et al. |
| 6,306,177 | B1 | 10/2001 | Felt et al. | 6,610,006 | B1 | 8/2003 | Amid et al. |

| | | | | | | |
|---|---|---|---|---|---|---|
| 6,610,071 B1 | 8/2003 | Cohn et al. | | 6,835,205 B2 | 12/2004 | Atkinson et al. |
| 6,610,079 B1 | 8/2003 | Li et al. | | 6,835,207 B2 | 12/2004 | Zacouto et al. |
| 6,610,091 B1 | 8/2003 | Reiley | | 6,835,208 B2 | 12/2004 | Marchosky |
| 6,610,666 B1 | 8/2003 | Akerblom | | 6,841,150 B2 | 1/2005 | Halvorsen et al. |
| 6,613,044 B2 | 9/2003 | Carl | | 6,843,799 B2 | 1/2005 | Bartlett |
| 6,620,185 B1 | 9/2003 | Harvie et al. | | 6,852,128 B2 | 2/2005 | Lange |
| 6,620,196 B1 | 9/2003 | Trieu | | 6,860,895 B1 | 3/2005 | Akerfeldt et al. |
| 6,623,492 B1 | 9/2003 | Berube et al. | | 6,878,155 B2 | 4/2005 | Sharkey et al. |
| 6,623,508 B2 | 9/2003 | Shaw et al. | | 6,878,167 B2 | 4/2005 | Ferree |
| 6,626,899 B2 | 9/2003 | Houser et al. | | 6,883,520 B2 | 4/2005 | Lambrecht et al. |
| 6,626,916 B1 | 9/2003 | Yeung et al. | | 6,893,462 B2 | 5/2005 | Buskirk et al. |
| 6,635,073 B2 | 10/2003 | Bonutti et al. | | 6,896,675 B2 | 5/2005 | Leung et al. |
| 6,645,227 B2 | 11/2003 | Fallin et al. | | 6,911,034 B2 | 6/2005 | Nobles et al. |
| 6,645,247 B2 | 11/2003 | Ferree | | 6,913,622 B2 | 7/2005 | Gjunter |
| 6,648,892 B2 | 11/2003 | Martello | | 6,923,823 B1 | 8/2005 | Bartlett et al. |
| 6,648,918 B2 | 11/2003 | Ferree | | 6,932,833 B1 | 8/2005 | Sandoval et al. |
| 6,648,919 B2 | 11/2003 | Ferree | | 6,936,070 B1 | 8/2005 | Muhanna |
| 6,648,920 B2 | 11/2003 | Ferree | | 6,936,072 B2 | 8/2005 | Lambrecht et al. |
| 6,652,561 B1 | 11/2003 | Tran | | 6,960,215 B2 | 11/2005 | Olson, Jr. et al. |
| 6,652,585 B2 | 11/2003 | Lange | | 6,964,674 B1 | 11/2005 | Matsuura et al. |
| 6,656,182 B1 | 12/2003 | Hayhurst | | 6,966,910 B2 | 11/2005 | Ritland |
| 6,669,687 B1 | 12/2003 | Saadat | | 6,966,931 B2 | 11/2005 | Huang |
| 6,669,707 B1 | 12/2003 | Swanstrom et al. | | 6,969,404 B2 | 11/2005 | Ferree |
| 6,669,729 B2 | 12/2003 | Chin | | 6,972,027 B2 | 12/2005 | Fallin et al. |
| 6,673,088 B1 | 1/2004 | Vargas et al. | | 6,974,479 B2 | 12/2005 | Trieu |
| 6,676,665 B2 | 1/2004 | Foley et al. | | 6,980,862 B2 | 12/2005 | Fredricks et al. |
| 6,679,887 B2 | 1/2004 | Nicholson et al. | | 6,984,241 B2 | 1/2006 | Lubbers et al. |
| 6,679,914 B1 | 1/2004 | Gabbay | | 6,984,247 B2 | 1/2006 | Cauthen |
| 6,684,886 B1 | 2/2004 | Alleyne | | 6,986,775 B2 * | 1/2006 | Morales et al. ............... 606/139 |
| 6,685,695 B2 | 2/2004 | Ferree | | 6,997,956 B2 | 2/2006 | Cauthen |
| 6,685,728 B2 | 2/2004 | Sinnott et al. | | 7,001,431 B2 | 2/2006 | Bao et al. |
| 6,689,125 B1 | 2/2004 | Keith et al. | | 7,004,959 B2 | 2/2006 | Bonutti |
| 6,692,506 B1 | 2/2004 | Ory et al. | | 7,004,970 B2 | 2/2006 | Cauthen |
| 6,695,858 B1 | 2/2004 | Dubrul et al. | | 7,033,393 B2 | 4/2006 | Gainor et al. |
| 6,696,073 B2 | 2/2004 | Boyce | | 7,033,395 B2 | 4/2006 | Cauthen |
| 6,699,263 B2 | 3/2004 | Cope | | 7,037,334 B1 | 5/2006 | Hlavka et al. |
| 6,706,068 B2 | 3/2004 | Ferree | | 7,052,516 B2 | 5/2006 | Cauthen, III et al. |
| 6,712,836 B1 | 3/2004 | Berg et al. | | 7,083,638 B2 | 8/2006 | Foerster |
| 6,712,837 B2 | 3/2004 | Akerfeldt et al. | | 7,094,258 B2 | 8/2006 | Lambrecht et al. |
| 6,712,853 B2 | 3/2004 | Kuslich | | 7,147,651 B2 | 12/2006 | Morrison et al. |
| 6,716,216 B1 | 4/2004 | Boucher et al. | | 7,189,235 B2 | 3/2007 | Cauthen |
| 6,719,761 B1 | 4/2004 | Reiley et al. | | 7,217,279 B2 | 5/2007 | Reese |
| 6,719,773 B1 | 4/2004 | Boucher et al. | | 7,223,289 B2 | 5/2007 | Trieu et al. |
| 6,719,797 B1 | 4/2004 | Ferree | | 7,280,865 B2 | 10/2007 | Adler |
| 6,723,058 B2 | 4/2004 | Li | | 7,285,124 B2 | 10/2007 | Foerster |
| 6,723,095 B2 | 4/2004 | Hammerslag | | 7,306,417 B2 | 12/2007 | Dorstewitz |
| 6,723,097 B2 | 4/2004 | Fraser et al. | | 7,309,337 B2 | 12/2007 | Colleran et al. |
| 6,723,107 B1 | 4/2004 | Skiba et al. | | 7,318,840 B2 | 1/2008 | McKay |
| 6,723,133 B1 | 4/2004 | Pajotin | | 7,320,701 B2 | 1/2008 | Haut et al. |
| 6,723,335 B1 | 4/2004 | Moehlenbruck et al. | | 7,322,978 B2 | 1/2008 | West, Jr. |
| 6,726,721 B2 | 4/2004 | Stoy et al. | | 7,329,272 B2 | 2/2008 | Burkhart et al. |
| 6,730,092 B2 | 5/2004 | Songer | | 7,331,982 B1 | 2/2008 | Kaiser et al. |
| 6,730,112 B2 | 5/2004 | Levinson | | 7,344,539 B2 | 3/2008 | Serhan et al. |
| 6,733,531 B1 | 5/2004 | Trieu | | 7,367,978 B2 | 5/2008 | Drewry et al. |
| 6,733,534 B2 | 5/2004 | Sherman | | 7,371,253 B2 | 5/2008 | Leung et al. |
| 6,736,815 B2 | 5/2004 | Ginn | | 7,390,332 B2 | 6/2008 | Selvitelli et al. |
| 6,740,093 B2 | 5/2004 | Hochschuler et al. | | 7,399,018 B1 | 7/2008 | Khachaturian |
| 6,743,255 B2 | 6/2004 | Ferree | | 7,445,634 B2 | 11/2008 | Trieu |
| 6,752,831 B2 | 6/2004 | Sybert et al. | | 7,465,308 B2 | 12/2008 | Sikora et al. |
| 6,758,863 B2 | 7/2004 | Estes | | 7,500,983 B1 | 3/2009 | Kaiser et al. |
| 6,761,720 B1 | 7/2004 | Senegas | | 7,513,911 B2 | 4/2009 | Lambrecht et al. |
| 6,761,722 B2 | 7/2004 | Cole et al. | | 7,524,333 B2 | 4/2009 | Lambrecht et al. |
| 6,764,514 B1 | 7/2004 | Li et al. | | 7,556,640 B2 | 7/2009 | Foerster |
| 6,767,037 B2 | 7/2004 | Wenstrom | | 7,611,521 B2 | 11/2009 | Lubbers et al. |
| 6,770,076 B2 | 8/2004 | Foerster | | 7,651,509 B2 | 1/2010 | Bojarski et al. |
| 6,773,436 B2 | 8/2004 | Donnelly et al. | | 7,749,273 B2 * | 7/2010 | Cauthen et al. ............ 623/17.11 |
| 6,773,699 B2 | 8/2004 | Soltz et al. | | 7,766,923 B2 | 8/2010 | Catanese et al. |
| 6,780,198 B1 | 8/2004 | Gregoire et al. | | 7,766,939 B2 | 8/2010 | Yeung et al. |
| 6,783,546 B2 | 8/2004 | Zuckerman et al. | | 8,100,141 B2 * | 1/2012 | Slupecki et al. ............... 137/456 |
| 6,805,695 B2 | 10/2004 | Keith et al. | | 8,128,698 B2 | 3/2012 | Bentley et al. |
| 6,805,697 B1 | 10/2004 | Helm et al. | | 8,163,022 B2 | 4/2012 | Bentley et al. |
| 6,805,715 B2 | 10/2004 | Reuter et al. | | 2002/0032483 A1 | 3/2002 | Nicholson et al. |
| 6,812,211 B2 | 11/2004 | Slivka et al. | | 2002/0077701 A1 | 6/2002 | Kuslich |
| 6,821,276 B2 | 11/2004 | Lambrecht et al. | | 2002/0082698 A1 | 6/2002 | Parenteau et al. |
| 6,824,562 B2 | 11/2004 | Mathis et al. | | 2002/0111688 A1 | 8/2002 | Cauthen |
| 6,827,716 B2 | 12/2004 | Ryan et al. | | 2002/0123807 A1 | 9/2002 | Cauthen, III |
| 6,827,743 B2 | 12/2004 | Eisermann et al. | | 2002/0147461 A1 | 10/2002 | Aldrich |
| 6,830,570 B1 | 12/2004 | Frey et al. | | 2002/0151979 A1 | 10/2002 | Lambrecht et al. |
| 6,833,006 B2 | 12/2004 | Foley et al. | | 2002/0173851 A1 | 11/2002 | McKay |

| | | |
|---|---|---|
| 2003/0074075 A1 | 4/2003 | Thomas |
| 2003/0125807 A1 | 7/2003 | Lambrecht et al. |
| 2003/0153976 A1 | 8/2003 | Cauthen, III et al. |
| 2003/0158604 A1 | 8/2003 | Cauthen et al. |
| 2003/0181983 A1 | 9/2003 | Cauthen |
| 2003/0195514 A1 | 10/2003 | Trieu et al. |
| 2003/0195628 A1 | 10/2003 | Bao et al. |
| 2003/0220649 A1 | 11/2003 | Bao et al. |
| 2003/0220690 A1 | 11/2003 | Cauthen, III |
| 2003/0220693 A1 | 11/2003 | Cauthen, III |
| 2003/0220694 A1 | 11/2003 | Cauthen, III |
| 2004/0039392 A1 | 2/2004 | Trieu |
| 2004/0054414 A1 | 3/2004 | Trieu |
| 2004/0097980 A1 | 5/2004 | Ferree |
| 2004/0260397 A1 | 12/2004 | Lambrecht et al. |
| 2005/0033363 A1 | 2/2005 | Bojarski et al. |
| 2005/0033440 A1 | 2/2005 | Lambrecht et al. |
| 2005/0038519 A1 | 2/2005 | Lambrecht et al. |
| 2005/0049592 A1 | 3/2005 | Keith et al. |
| 2005/0049704 A1 | 3/2005 | Jackson |
| 2005/0049708 A1 | 3/2005 | Atkinson et al. |
| 2005/0060038 A1 | 3/2005 | Sammartin |
| 2005/0149197 A1 | 7/2005 | Cauthen |
| 2005/0234512 A1 | 10/2005 | Nakao |
| 2005/0256582 A1 | 11/2005 | Ferree |
| 2005/0283246 A1 | 12/2005 | Cauthen, III et al. |
| 2006/0060038 A1 | 3/2006 | Sammartin |
| 2006/0084994 A1 | 4/2006 | Atkinson et al. |
| 2006/0100711 A1 | 5/2006 | Cauthen |
| 2006/0129156 A1 | 6/2006 | Cauthen, III et al. |
| 2006/0129245 A1 | 6/2006 | Cauthen |
| 2006/0142864 A1 | 6/2006 | Cauthen |
| 2006/0161258 A1 | 7/2006 | Cauthen |
| 2006/0167553 A1 | 7/2006 | Cauthen |
| 2006/0173545 A1 | 8/2006 | Cauthen |
| 2006/0190042 A1 | 8/2006 | Stone et al. |
| 2006/0190085 A1 | 8/2006 | Cauthen |
| 2006/0241773 A1 | 10/2006 | Cauthen |
| 2006/0253152 A1 | 11/2006 | Evans et al. |
| 2006/0287731 A1 | 12/2006 | Cauthen, III et al. |
| 2007/0061012 A1 | 3/2007 | Cauthen, III |
| 2007/0061013 A1 | 3/2007 | Cauthen III et al. |
| 2007/0071568 A1 | 3/2007 | Dorstewitz |
| 2007/0073407 A1 | 3/2007 | Cauthen et al. |
| 2007/0083236 A1 | 4/2007 | Sikora et al. |
| 2007/0088438 A1 | 4/2007 | Cauthen, III et al. |
| 2007/0100348 A1 | 5/2007 | Cauthen, III et al. |
| 2007/0100354 A1 | 5/2007 | Cauthen, III et al. |
| 2007/0118226 A1 | 5/2007 | Lambrecht et al. |
| 2007/0156244 A1 | 7/2007 | Cauthen |
| 2007/0156245 A1 | 7/2007 | Cauthen, III et al. |
| 2007/0185497 A1 | 8/2007 | Cauthen et al. |
| 2007/0198021 A1 | 8/2007 | Wales |
| 2007/0225814 A1 | 9/2007 | Atkinson et al. |
| 2007/0225815 A1 | 9/2007 | Keith et al. |
| 2007/0225816 A1 | 9/2007 | Keith et al. |
| 2007/0233257 A1 | 10/2007 | Keith et al. |
| 2007/0239280 A1 | 10/2007 | Keith et al. |
| 2007/0288041 A1 | 12/2007 | Cauthen |
| 2008/0033561 A1 | 2/2008 | Cauthen |
| 2008/0082128 A1 | 4/2008 | Stone |
| 2008/0140092 A1 | 6/2008 | Stone et al. |
| 2008/0255613 A1 | 10/2008 | Kaiser et al. |
| 2009/0024165 A1 | 1/2009 | Ferree |
| 2009/0259260 A1 | 10/2009 | Bentley et al. |
| 2009/0318961 A1 | 12/2009 | Stone et al. |
| 2011/0172682 A1 | 7/2011 | Brady et al. |

FOREIGN PATENT DOCUMENTS

| | | |
|---|---|---|
| EP | 0 025 706 | 3/1981 |
| EP | 0 042 953 | 1/1982 |
| EP | 0 049 978 | 4/1982 |
| EP | 0 076 409 | 4/1983 |
| EP | 0 110 316 | 6/1984 |
| EP | 0 122 902 | 10/1984 |
| EP | 0 126 570 | 11/1984 |
| EP | 0 145 577 | 6/1985 |
| EP | 0 193 784 | 9/1986 |
| EP | 1 797 827 | 6/2007 |
| EP | 1 857 055 | 11/2007 |
| GB | 2 054 383 | 2/1981 |
| WO | WO 91/16867 | 11/1991 |
| WO | WO 94/23671 | 10/1994 |
| WO | WO 95/22285 | 8/1995 |
| WO | WO 95/31946 | 11/1995 |
| WO | WO 95/31948 | 11/1995 |
| WO | WO 96/27339 | 9/1996 |
| WO | WO 97/20874 | 6/1997 |
| WO | WO 97/26847 | 7/1997 |
| WO | WO 98/01091 | 1/1998 |
| WO | WO 98/05274 | 2/1998 |
| WO | WO 98/22050 | 5/1998 |
| WO | WO 98/20939 | 9/1998 |
| WO | WO 99/00074 | 1/1999 |
| WO | WO 99/02108 | 1/1999 |
| WO | WO 99/04720 | 2/1999 |
| WO | WO 99/16381 | 4/1999 |
| WO | WO 99/61084 | 12/1999 |
| WO | WO 00/20021 | 4/2000 |
| WO | WO 00/25706 | 5/2000 |
| WO | WO 00/42953 | 7/2000 |
| WO | WO 00/49978 | 8/2000 |
| WO | WO 00/61037 | 10/2000 |
| WO | WO 00/62832 | 10/2000 |
| WO | WO 00/76409 | 12/2000 |
| WO | WO 01/10316 | 2/2001 |
| WO | WO 01/12107 | 2/2001 |
| WO | WO 01/21246 | 3/2001 |
| WO | WO 01/22902 | 4/2001 |
| WO | WO 01/26570 | 4/2001 |
| WO | WO 01/28464 | 4/2001 |
| WO | WO 01/45577 | 6/2001 |
| WO | WO 01/93784 | 12/2001 |
| WO | WO 01/95818 | 12/2001 |
| WO | WO 02/17825 | 3/2002 |
| WO | WO2009100242 A2 | 8/2009 |

OTHER PUBLICATIONS

Partial Internal Search Report issued in PCT/US2011/020699, mailed Mar. 24, 2011, 6 pages.

* cited by examiner

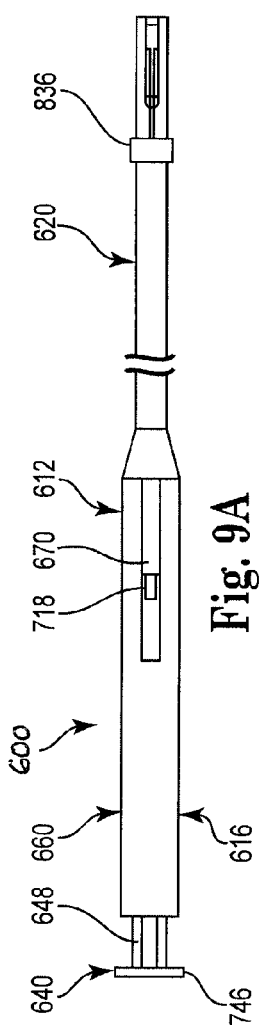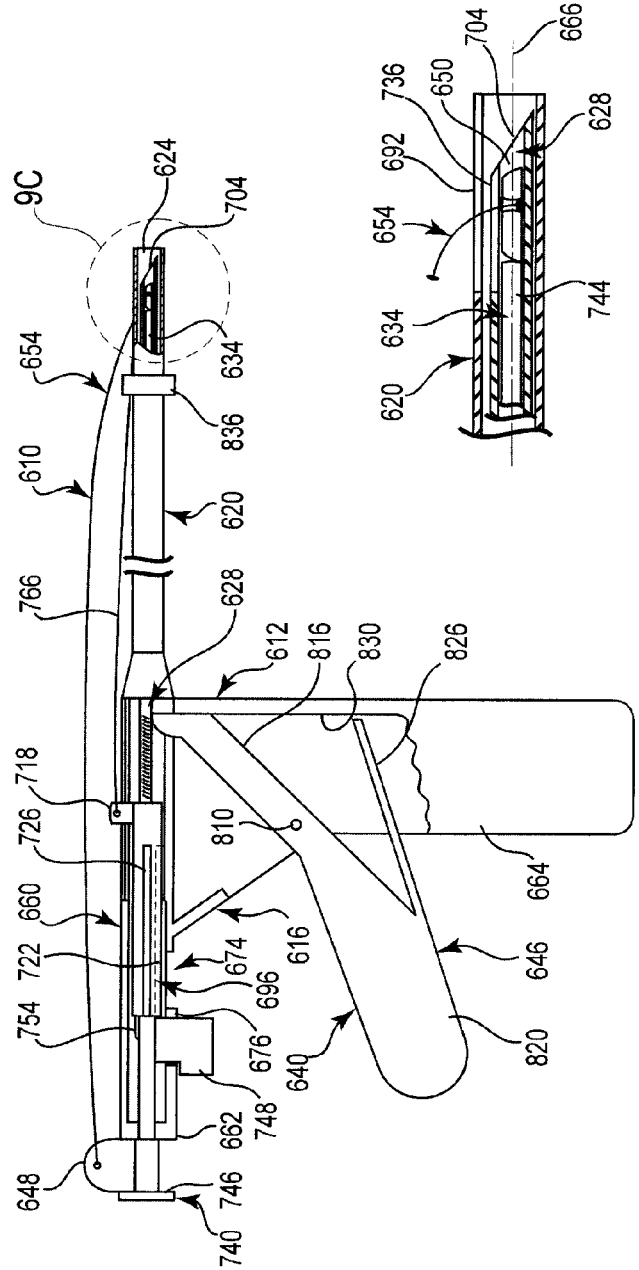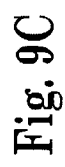

INTERVERTEBRAL DISC ANNULUS REPAIR SYSTEM AND METHOD

CROSS-REFERENCE TO RELATED APPLICATION

This application claims the benefit of U.S. Provisional Application Nos. 61/293,939, Filed Jan. 11, 2010, and 61/323,679 filed Apr. 13, 2010, the disclosures of which are incorporated herein by reference in their entireties.

TECHNICAL FIELD

The invention generally relates to methods and devices for the closure, sealing, repair and/or reconstruction of an intervertebral disc annulus, and accompanying delivery devices and tools, and their methods of use.

BACKGROUND

The spinal column is formed from a number of bony vertebrae, which in their normal state are separated from each other by intervertebral discs. These discs are comprised of the annulus fibrosus, and the nucleus pulposus, both of which are soft tissue. The intervertebral disc acts in the spine as a crucial stabilizer, and as a mechanism for force distribution between adjacent vertebral bodies. Without a competent disc, collapse of the intervertebral disc may occur, contributing to abnormal joint mechanics and premature development of degenerative and/or arthritic changes.

The normal intervertebral disc has an outer ligamentous ring called the annulus surrounding the nucleus pulposus. The annulus binds the adjacent vertebrae together and is constituted of collagen fibers that are attached to the vertebrae and cross each other so that half of the individual fibers will tighten as the vertebrae are rotated in either direction, thus resisting twisting or torsional motion. The nucleus pulposus is constituted of soft tissue, having about 85% water content, which moves about during bending from front to back and from side to side.

The aging process contributes to gradual changes in the intervertebral discs. Fissures in the annulus fibrosus can occur due to various causes, including disease or other pathological conditions, or the natural aging process. Occasionally fissures may form rents through the annular wall. In these instances, the nucleus pulposus is urged outwardly from the subannular space through a rent, often into the spinal column. Extruded nucleus pulposus can, and often does, mechanically press on the spinal cord or spinal nerve rootlet. This painful condition is clinically referred to as a ruptured or herniated disc.

In the event of annulus rupture, the subannular nucleus pulposus migrates along the path of least resistance forcing the fissure to open further, allowing migration of the nucleus pulposus through the wall of the disc, with resultant nerve compression and leakage of chemicals of inflammation into the space around the adjacent nerve roots supplying the extremities, bladder, bowel and genitalia. The usual effect of nerve compression and inflammation is intolerable back or neck pain, radiating into the extremities, with accompanying numbness, weakness, and in late stages, paralysis and muscle atrophy, and/or bladder and bowel incontinence. Additionally, injury, disease or other degenerative disorders may cause one or more of the intervertebral discs to shrink, collapse, deteriorate or become displaced, herniated, or otherwise damaged and compromised.

SUMMARY

The various embodiments of the present invention relate to system for intervertebral disc annulus repair. Accordingly, Example 1 of the present invention is a device for at least partially closing an aperture in an annulus fibrosus of an intervertebral disc of a patient, the device comprising an implant delivery tool and an implant releasably coupled to the implant delivery tool. The implant delivery tool includes a substantially rigid outer tube having a proximal section and a sharpened distal tip, a body coupled to the proximal section of the outer tube, and a plunger assembly movable axially relative to the body and including a plunger member and a pusher tube coupled thereto and disposed within the outer tube. The implant includes first and second tissue anchors serially disposed within the distal section of the outer tube, and a flexible connecting element coupling the first and second tissue anchors, the connecting element at least partially formed from a braided tubular suture material. The braided suture material includes a distal segment attached to the first tissue anchor, an intermediate segment extending proximally from the distal segment and including a locking element and an adjustable loop, wherein a portion of the intermediate segment extends internally within the braided suture material of the locking element, and wherein the second tissue anchor is slidably coupled to the braided suture material of the adjustable loop, and a proximal segment of the braided suture material extending proximally from the intermediate segment and releasably coupled to the implant delivery tool.

In Example 2, the device of Example 1 wherein the pusher tube is displaceable within the outer tube from a first position to a second position to eject the first tissue anchor from the outer tube.

In Example 3, the device of Example 1 or 2 wherein the pusher tube is further displaceable within the outer tube from the second position to a third position to eject the second tissue anchor from the outer tube.

In Example 4, the device of any of Examples 1 through 3 wherein the implant delivery tool includes a releasable tab releasably coupled to the plunger assembly.

In Example 5, the device of Example 4 wherein the connecting element is partially disposed within the outer tube and the proximal segment of the flexible connecting element is coupled to the releasable tab of the implant delivery tool.

The present invention, according to Example 6, is an implant for at least partially closing an aperture in an annulus fibrosus of an intervertebral disc of a patient. The implant comprises first and second tissue anchors sized and shaped to be disposed in a tubular member of a delivery tool and to be inserted into or through a portion of the annulus fibrosus, and a flexible connecting element coupling the first and second tissue anchors. The connecting element is at least partially formed from a tubular braided suture material and includes a distal segment of the braided suture material attached to the first tissue anchor, an intermediate segment of the braided suture material extending proximally from the distal segment and including a locking element and an adjustable loop, wherein a portion of the intermediate segment extends internally within the braided suture material of the locking element, and wherein the second tissue anchor is slidably coupled to the braided suture material of the adjustable loop, and a proximal segment of the braided material extending proximally from the intermediate segment and operable by a user to be placed in tension to reduce the length of the adjustable loop.

The present invention, in Example 7, is a device for at least partially closing an aperture in an annulus fibrosus of an intervertebral disc of a patient, the device comprising an implant delivery tool and an implant releasably coupled to the implant delivery tool. The implant delivery tool includes a substantially rigid outer tube having a proximal section, an intermediate section, and a distal section terminating in a sharpened tissue-piercing distal tip having an open end. The intermediate section has a first length, wherein the proximal and distal sections are laterally offset from one another by the intermediate section. The implant delivery tool further includes a body coupled to the proximal section of the outer tube, a plunger assembly including a plunger member slidably disposed within the body, and a pusher tube slidably disposed within the body and the outer tube and coupled to the plunger member. The pusher tube includes a distal end and a flexible segment proximal to the distal end axially coincident with the intermediate portion of the outer tube. The flexible segment has a second length greater than the first length of the intermediate portion of the outer tube. The implant includes a pair of tissue anchors serially disposed within the distal section of the outer tube, and an adjustable flexible connecting element connecting the tissue anchors. The plunger assembly is operable by a user to selectively displace the pusher tube distally within the outer tube so as to serially eject the first tissue anchor and then the second tissue anchor from the open end of the outer tube.

In Example 8, the device of Example 7 wherein the pusher tube is displaceable within the outer tube from a first position to a second position to eject the first tissue anchor from the outer tube.

In Example 9, the device of Example 8 wherein the pusher tube is further displaceable within the outer tube from the second position to a third position to eject the second tissue anchor from the outer tube.

In Example 10, the device of Examples 8 or 9 wherein the intermediate section of the outer tube is axially coincident with at least a portion of the flexible segment of the pusher tube when the pusher tube is in the first, the second and the third positions.

In Example 11, the device of any of Examples 7 through 10 wherein the implant delivery tool includes a releasable tab coupled to the plunger assembly.

In Example 12, the device of Example 11 wherein a first portion of the connecting element is disposed within the outer tube and a second portion of the flexible connecting element is coupled to the releasable tab of the implant delivery tool.

In Example 13, the device of any of Examples 7 through 12 wherein the flexible connecting element has an adjustable length so as to allow separation between the tissue anchors to be reduced after deployment.

In Example 14, the device of any of Examples 7 through 13 wherein the flexible connecting element is a knotless suture arrangement including a locking element substantially preventing elongation of the flexible connecting element between the tissue anchors after deployment.

In Example 15, the device of any of Examples 7 through 14 wherein the flexible segment of the pusher tube includes a series of slots extending circumferentially about the pusher tube in a helical pattern, the slots imparting lateral flexibility to the flexible segment.

In Example 16, the device of Example 15 wherein the slots have an undulating shape.

In Example 17, the device of any of Examples 7 through 14 wherein the flexible segment of the pusher tube is heat treated to impart lateral flexibility to the flexible segment.

In Example 18, the device of any of Examples 7 through 14 wherein the flexible segment of the pusher tube is in the form of a helical spring.

In Example 19, the device of any of Examples 7 through 18 wherein the proximal and distal sections of the outer tube are substantially parallel to one another.

In Example 20, the device of any of Examples 7 through 19 wherein the intermediate section of the outer tube has a first curved portion extending from the proximal section and a second curved portion extending proximally from the distal section having an opposite curvature to that of the first curved portion.

The present invention, according to Example 21, is a device for at least partially closing an aperture in an annulus fibrosus of an intervertebral disc of a patient, the device comprising an implant delivery tool and an implant releasably coupled to the implant delivery tool. The implant delivery tool includes a substantially rigid outer tube having a proximal section, a distal section, and an intermediate section having a non-linear shape laterally offsetting the proximal and distal sections from one another. The implant delivery tool further includes a body coupled to the proximal section of the outer tube, a plunger assembly movable axially relative to the body and including a plunger member and a pusher tube coupled thereto and disposed within the outer tube. The pusher tube has a substantially rigid proximal segment, a substantially rigid distal segment including a distal end, and a flexible segment between the proximal and distal segments. The pusher tube is slidably displaceable within the outer tube to assume a plurality of positions, and the flexible segment is configured to conform to the nonlinear shape of the intermediate section of the outer tube in each of the plurality of positions of the pusher tube. The implant includes a pair of tissue anchors serially disposed within the distal section of the outer tube, and an adjustable flexible connecting element connecting the tissue anchors.

In Example 22, the device of Example 21 wherein the flexible segment of the pusher tube is dimensioned such that the intermediate section of the outer tube is axially coincident with at least a portion of the flexible segment in each of the plurality of positions of the pusher tube.

In Example 23, the device of Example 21 or 22 wherein the proximal and distal sections of the outer tube are substantially parallel to one another.

In Example 24, the device of any of Examples 21 through 23 wherein the adjustable flexible connecting element is a knotless suture arrangement including a locking element substantially preventing elongation of the flexible connecting element between the tissue anchors after deployment.

In Example 25, the device of any of Examples 21 through 24 wherein the flexible segment of the pusher tube includes a series of slots extending circumferentially about the pusher tube in a helical pattern, the slots imparting lateral flexibility to the flexible segment.

The present invention, according to Example 26, is a system for at least partially closing an aperture in an annulus fibrosus of an intervertebral disc of a patient, the system comprising first and second repair devices each including an implant delivery tool and an implant releasably coupled to the implant delivery tool including. The implant delivery tool includes a substantially rigid outer tube having a proximal section and a distal section terminating in a sharpened distal tip, a body coupled to the proximal section of the outer tube, and a plunger assembly movable axially relative to the body and including a pusher tube disposed within the outer tube, wherein the pusher tube is slidably displaceable within the outer tube to assume a plurality of positions. The implant includes first and second tissue anchors serially disposed within the distal section of the outer tube, and a flexible connecting element coupling the first and second tissue anchors. The flexible connecting element is at least partially formed from a braided tubular suture material and includes a distal segment of the braided suture material attached to the first tissue anchor, an intermediate segment of the braided suture material extending proximally from the distal segment and including a locking element and an adjustable loop, wherein a portion of the intermediate segment extends internally within the braided suture material of the locking element, and wherein the second tissue anchor is slidably coupled to the braided suture material of the adjustable loop, and a proximal segment of the braided suture material extending proximally from the intermediate segment and releasably coupled to the implant delivery tool.

The present invention, according to Example 27, is an instrument for use in implanting a suture assembly. The instrument comprises a body having longitudinal axis, a first end, and a second end. The first end has a canted tip and a first slot therein sized to slidingly receive a portion of the suture assembly. The second end has a tip with a second slot therein sized to receive a portion of the suture assembly. The instrument further comprises a recessed blade with a cutting edge exposed within the second slot. The cutting edge is configured to cut the suture assembly.

In Example 28, the instrument of Example 27 wherein the cutting edge of the blade is oriented toward the tip of the second end of the body.

In Example 29, the instrument of either of Examples 27 or 28 wherein at least a portion of the blade is oriented at an angle to the longitudinal axis.

In Example 30, the instrument of any of Examples 27 through 29 wherein the blade includes a coating.

In Example 31, the instrument of Example 30 wherein the coating includes titanium nitride.

The present invention, according to Example 32, is an implant for use in an orthopedic repair procedure to repair a tissue defect. The implant comprises first and second tissue anchors and a flexible connecting element. The first and second tissue anchors are sized and shaped to be disposed in a tubular member of a delivery tool and to be inserted into or through tissue proximate the defect. The flexible connecting element couples the first and second tissue anchors and is at least partially formed from a tubular braided suture material. The connecting element includes a distal segment of the braided suture material attached to the first tissue anchor, an intermediate segment of the braided suture material extending proximally from the distal segment and including a locking element and an adjustable loop, wherein a portion of the intermediate segment extends internally within the braided suture material of the locking element, and wherein the second tissue anchor is slidably coupled to the braided suture material of the adjustable loop. The connecting element further includes a a proximal segment of the braided material extending proximally from the intermediate segment and operable by a user to be placed in tension to reduce the length of the adjustable loop.

The present invention, according to Example 34, is an intervertebral disc repair system comprising an implant and a delivery tool. The implant includes an anchor member and an adjustable suture assembly coupled thereto. The adjustable suture assembly forms an adjustable loop and includes a tension line having a proximal end, and a toggle line coupled to the anchor member for selectively rotating the anchor member during deployment thereof. The delivery tool includes a proximal handle, an outer tubular member, a needle cannula, an inner pusher member, and an actuating mechanism. The outer tubular member extends distally from the handle and has an open distal end. The needle cannula is slidably received within the outer tubular member and has a proximal portion with a proximal end, and an open distal end terminating with a sharpened tip for penetrating tissue. The inner pusher member is slidably received within the needle cannula and has a proximal end and a distal end. The actuating mechanism is coupled to the handle for selectively retracting the needle cannula relative to the outer tubular member and the inner pusher member. The proximal end of the tension line of the implant is operable by the user to reduce at least one dimension of the loop. The anchor member and at least a portion of the adjustable suture assembly of the implant are releasably received within the needle cannula distal to the distal end of the inner pusher member. The delivery tool is configured such that actuation of the actuating mechanism proximally retracts the needle cannula relative to the outer tubular member and the inner pusher member to release the anchor member from the needle cannula, and the toggle line of the adjustable suture assembly of the implant is operable to cause rotation of the anchor member as the anchor member is released from the needle cannula.

In Example 35, the system of Example 34 wherein the delivery tool is configured such that the needle cannula and the inner pusher member can be axially advanced together relative to the outer tubular member.

In Example 36, the system of Examples 34 or 35 wherein the delivery tool is configured such that the needle cannula is retractable relative to the inner pusher member upon actuation of the actuating member after axially advancing the needle cannula and the inner pusher member relative to the outer tubular member.

In Example 37, the system of any of Examples 34 through 36 wherein the delivery tool is configured to prevent proximal movement of the inner pusher member upon retraction of the needle cannula relative to the inner pusher member and the outer tubular member.

In Example 38, the system of any of Examples 34 through 37 wherein the adjustable suture assembly includes a knotless locking element configured to prevent elongation of the adjustable loop.

In Example 39, the system of any of Examples 34 through 38 wherein the handle of the delivery tool includes a tubular upper portion having a proximal end, and a lower portion extending from the upper portion adapted to be gripped by the user, wherein the outer tubular member extends distally from the tubular upper portion of the handle such that the upper portion of the handle and the outer tubular member define a longitudinal axis of the delivery tool, and wherein the needle cannula and the inner pusher member of the delivery tool are aligned with the longitudinal axis.

In Example 40, the system of any of Examples 34 through 39 wherein the proximal end of the inner pusher member further includes an end plate extending radially from the inner pusher member.

In Example 41, the system of any of Examples 34 through 40 wherein the delivery tool includes a releasable tab coupled to the proximal end of the second implant tension line, the releasable tab operable by the user to apply tension to the tension line to reduce the at least one dimension of the loop, the releasable tab further releasably coupled to the inner pusher member between the end plate and the proximal end of the upper portion of the handle preventing axial movement of the inner pusher member.

In Example 42, the system of any of Examples 34 through 41 wherein the proximal portion of the needle cannula further includes a flange having an aperture therein, and wherein the toggle line has a proximal end portion connected to the flange.

In Example 43, the system of any of Examples 34 through 42 wherein the delivery tool is further configured such that actuation of the actuating mechanism proximally retracts the needle cannula thereby applying tension to the toggle line to rotate the anchor member as the anchor member is released from the needle cannula.

In Example 44, an intervertebral disc repair system for repairing a defect in an intervertebral disc of a patient, the system comprising a first implant and a first delivery tool, and a second implant and a second delivery tool. The first implant includes first and second tissue anchors, and an adjustable connecting element connecting the first and second tissue anchors, the adjustable connecting element having an adjustable length between the first and second tissue anchors. The first delivery tool includes a tissue penetrating tubular member, the first and second tissue anchors releasably received in the tubular member, the first delivery tool configured to deploy the first and second tissue anchors in the intervertebral disc. The second implant includes an anchor member and an adjustable suture assembly coupled thereto, the adjustable suture assembly forming an adjustable loop and including a tension line having a proximal end operable by a user to reduce at least one dimension of the adjustable loop, and a toggle line coupled to the anchor member for rotating the anchor member during deployment thereof. The second delivery tool includes a proximal handle, an outer tubular member, a needle cannula, an inner pusher member, and an actuating mechanism. The outer tubular member extends distally from the handle and has an open distal end. The needle cannula is slidably received within the outer tubular member and has a proximal portion with a proximal end and an open distal end terminating with a sharpened tip for penetrating tissue. The inner pusher member is slidably received within the needle cannula and has a proximal end and a distal end. The actuating mechanism is coupled to the handle for selectively adjusting an axial position of the needle cannula relative to the outer tubular member and the inner pusher member. The anchor member and at least a portion of the adjustable suture assembly of the second implant are releasably received within the needle cannula of the second delivery tool. The toggle line of the adjustable suture assembly of the second implant is operable to cause rotation of the anchor member during deployment thereof upon actuation of the actuating mechanism by a user. The adjustable suture assembly and the connecting element are configured to be interconnected and placed under tension after deployment of the anchor member and the first and second tissue anchors.

In Example 45, the system of Example 44 wherein the second delivery tool is configured such that the needle cannula and the inner pusher member can be axially advanced together relative to the outer tubular member.

In Example 46, the system of Examples 44 or 45 wherein the second delivery tool is further configured such that the needle cannula is retractable relative to the inner pusher member upon actuation of the actuating member after axially advancing the needle cannula and the inner pusher member relative to the outer tubular member.

In Example 47, the system of any of Examples 44 through 46 wherein the second delivery tool is configured to prevent proximal movement of the inner pusher member during retraction of the needle cannula relative to the inner pusher member and the outer tubular member so as to cause the anchor member to be released from the needle cannula.

In Example 48, the system of any of Examples 44 through 47 wherein the second delivery tool includes a releasable tab coupled to the proximal end of the second implant tension line, the releasable tab operable by the user to apply tension to the tension line to reduce the at least one dimension of the loop.

In Example 49, the system of any of Examples 44 through 48 wherein the second delivery tool is configured such that actuation of the actuating mechanism proximally retracts the needle cannula relative to the outer tubular member and the inner pusher member to release the anchor member from the needle cannula.

In Example 50, the system of any of Examples 44 through 49 wherein the proximal portion of the needle cannula of the second delivery tool further includes a flange having an aperture therein, and wherein the toggle line has a proximal end portion connected to the flange.

In Example 51, the system of any of Examples 44 through 50 wherein the second delivery tool is further configured such that actuation of the actuating mechanism proximally retracts the needle cannula thereby applying tension to the toggle line as the anchor member is released from the needle cannula.

In Example 51, the system of any of Examples 447 through 51 wherein the handle of the second delivery tool includes a tubular upper portion having a proximal end and a lower portion extending from the upper portion adapted to be gripped by the user, wherein the outer tubular member extends distally from the tubular upper portion of the handle such that the upper portion of the handle and the outer tubular member define a longitudinal axis of the second delivery tool, and wherein the needle cannula and the inner pusher member of the second delivery tool are aligned with the longitudinal axis.

In Example 53, the system of any of Examples 44 through 52 wherein the proximal end of the inner pusher member extends proximally from the upper portion of the second delivery tool handle.

In Example 54, the system of any of Examples 44 through 53 wherein the proximal end of the inner pusher member further includes an end plate extending radially from the inner pusher member relative to the longitudinal axis.

In Example 55, the system of any of Examples 44 through 54 wherein the releasable tab is releasably coupled to the inner pusher member between the end plate and the proximal end of the upper portion of the handle preventing axial movement of the inner pusher member.

In Example 56, the system of any of Examples 44 through 55 further comprising a tension guide including a first end having a canted tip and a first slot therein sized to slidingly receive portions of the connecting element of the first implant and the suture assembly of the second implant, and a second end having a tip with a second slot therein, and a recessed blade with a cutting edge exposed within the second slot. The second slot is sized to slidingly receive portions of the connecting element of the first implant and the suture assembly of the second implant. The cutting edge is configured to cut the connecting element and the suture assembly to remove excess portions thereof.

In Example 57, the system of Example 56 wherein the cutting edge of the tension guide blade is oriented toward the tip of the second end of the tension guide.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 9A-9C are plan and partial cut-away elevation views of an implant delivery tool with an implant coupled thereto according to one embodiment of the present invention.

Figure 1:
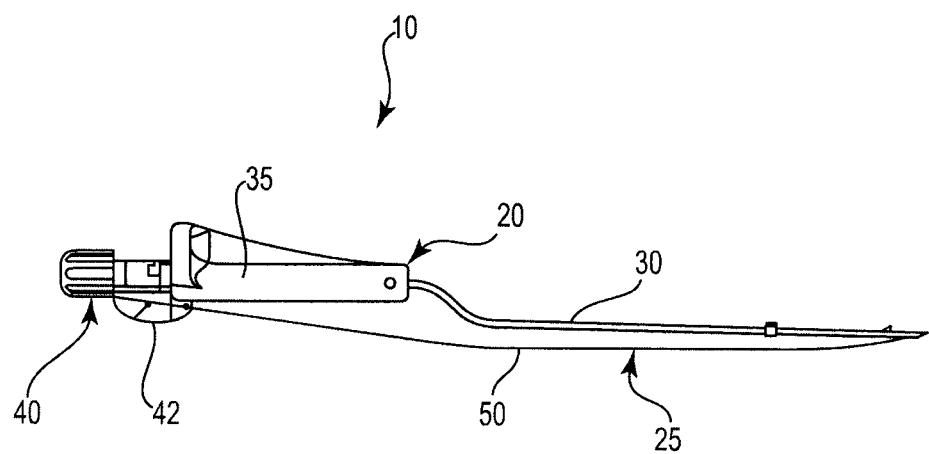
FIG. 1 illustrates a device for use in repairing an aperture or a defect in an annulus fibrosus of an intervertebral disc according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 illustrates a repair device 10 for use in repairing an aperture or a defect in an annulus fibrosus of an intervertebral disc according to an embodiment of the present invention. As shown in FIG. 1, the repair device 10 includes an implant delivery tool 20 and an implant 25 coupled thereto for deployment in intervertebral disc tissue. As further shown, the implant delivery tool 20 includes an outer tube 30, a body 35, a plunger assembly 40, and a releasable tab 42. In the illustrated embodiment, the body 35 is fixedly attached to the outer tube 30, and the plunger assembly 40 is partially disposed within the body 35. The tab 42 is releasably coupled to the plunger assembly 40. The implant delivery tool 20 is configured such that the outer tube 30 can be partially inserted into soft tissues of the intervertebral disc (e.g., the annulus fibrosus) for delivery of the implant 25, with the plunger assembly 40 being configured to facilitate deployment of the implant.

As shown and described in further detail below, the implant 25 is partially disposed within a portion of the implant delivery tool 20 prior to deployment. Additionally, the implant 25 includes a tension line 50 extending external to the outer tube 30 and connected to the tab 42. The implant 25 is configured to facilitate full or partial closure of an aperture (e.g., a defect resulting from a herniated and ruptured annulus, or an opening from an incision made by a physician in a discectomy procedure) by drawing together the annulus fibrosus tissues defining the aperture under tension (i.e., re-approximating the annulus fibrosus). The tab 42 is positioned, in the undeployed state of FIG. 1, so as to prevent spontaneous axial movement of the plunger assembly 40 and, in turn, unintended deployment of the implant 25. Additionally, the tension line 50 is connected to the tab 42, which can be manipulated by the user to apply tension to the tension line 50 to facilitate final deployment of the implant 25 (as discussed in further detail below).

Figure 2A:
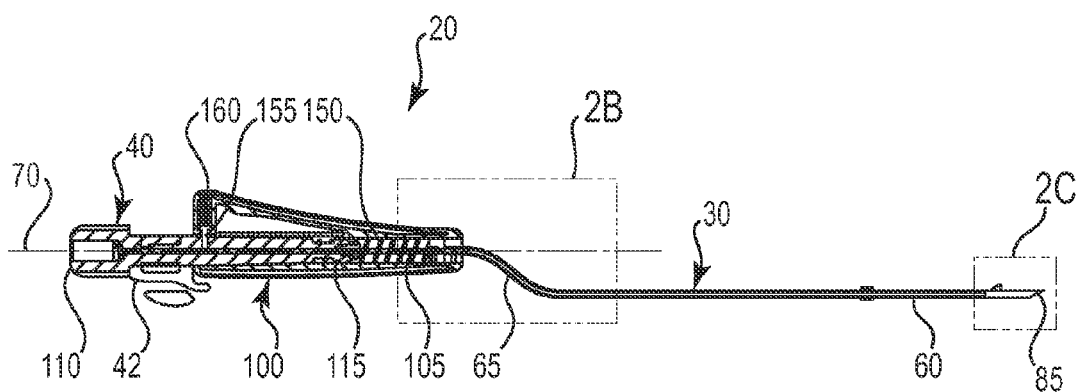
FIGS. 2A, 2B and 2C are partial cutaway views of an implant delivery tool of the device of FIG. 1 according to one embodiment of the present invention.
Figure 2B:
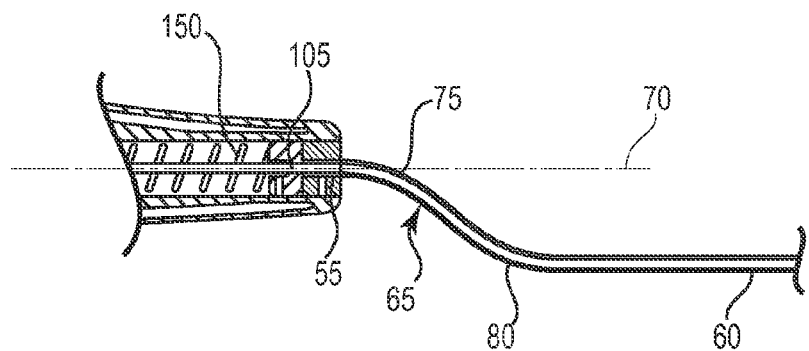
Figure 2C:
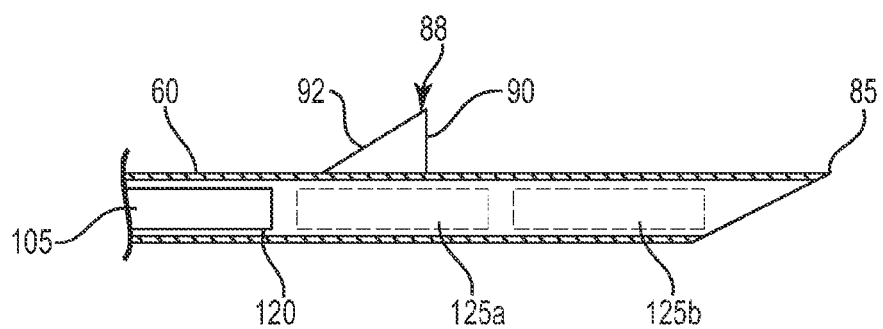

FIGS. 2A, 2B and 2C are partial cutaway views of an implant delivery tool 20 of the repair device 10 of FIG. 1 according to one embodiment of the present invention. As shown in FIGS. 2A-2C, the outer tube 30 has a proximal section 55, a distal section 60 and an intermediate section 65 between the proximal and distal sections 55, 60. As further shown, the proximal section 55 is fixedly disposed within the body 35 and extends generally along a line parallel to a longitudinal axis 70 defined by the body 35 and the plunger assembly 40.

In the illustrated embodiment, the intermediate section 65 includes a proximal curved portion 75 and a distal curved portion 80 having an opposite curvature to that of the proximal curved portion 75. Additionally, as shown, the distal section 60 also extends distally from the distal curved portion 80 along a line generally parallel to the longitudinal axis 70. Accordingly, as can be seen in FIGS. 2A and 2B, the proximal and distal sections 55, 60 are laterally offset from one another by the intermediate section 65. In the illustrated embodiment, the proximal and distal sections 55, 60 are generally parallel to one another, although in other embodiments these sections may be angularly offset from one another as well.

As further shown, distal section 60 of the outer tube 30 terminates in a sharpened, tissue-piercing distal tip 85 and includes a tissue stop 88. The distal tip 85 is configured to penetrate intervertebral disc tissue, in particular, the annulus fibrosus, for deployment of the implant 25, with the tissue stop 88 operating to delimit the depth of penetration of the outer tube 30 into the disc tissue. The tissue stop 88 attached to the outer surface of the outer tube 30 and is located proximally a predetermined distance from the distal tip 85. In the illustrated embodiment, the tissue stop 88 includes a blunt distal face 90 and a sloped proximal face 92, which is shaped to substantially prevent the proximal face 92 from catching on tissues when retracting the outer tube 30 from the annulus fibrosus. In other embodiments, other structures (e.g., an enlarged diameter segment of the outer tube 30) suitable for delimiting the penetration of the outer tube 30, are provided.

As shown and discussed in further detail below, laterally offsetting the proximal and distal sections 55, 60 of the outer tube 30 advantageously improves the physician's visualization of the affected area of the annulus fibrosus to be repaired. That is, it allows the physician to manipulate the implant delivery tool 30, and in particular, the body 35 and the plunger assembly 40 without having his or her hands interfere with the line of sight to the aperture in the annulus fibrosus.

As further shown in FIGS. 2A-2C, the plunger assembly 40 includes a plunger member 100 and a pusher tube 105. As illustrated, the plunger member 100 includes a proximal knob 110 and a distal portion 115 extending therefrom. Additionally, the distal portion 115 of the plunger member 100 is slidably and partially rotatably disposed within the body 35. The pusher tube 105 is fixedly connected to and extends distally from the distal portion 115 of the plunger member 100 within the outer tube 30, terminating in a distal end 120. Accordingly, the pusher tube 105 is also slidably and rotatably disposed within the outer tube 30.

The implant delivery tool 20 may, in many respects, have the same general functionality as, for example, the fixation delivery apparatus 400 described above and illustrated in FIGS. 48A-48E of co-pending and commonly assigned U.S. Patent Publication No. 2009/0259260, the disclosure of which is incorporated herein by reference in its entirety. Thus, the plunger assembly 40 is slidable relative to the body 35 and the outer tube 30 to effectuate axial movement of the pusher tube 105 for ejecting the implant 25 from the outer tube 30 into the desired implantation location within the disc annulus. In various embodiments, the implant delivery tool 20 further includes additional features that allow the plunger member 100 and, in turn the pusher tube 105, to assume a plurality of discrete positions relative to outer tube 30 to selectively eject portions of the implant 25 therefrom.

For example, in various embodiments, the implant 25 includes two or more soft tissue anchors 125a, 125b (shown in dashed lines in FIG. 2C) disposed in the distal section 60 of the outer tube 30 prior to deployment, with the distal end 120 of the pusher tube 105 positioned just proximal to or abutting the proximal-most tissue anchor 125a. As will be apparent from FIGS. 2A and 2C, by selectively advancing the plunger member 100 distally within the body 35 (after removing the tab 42 from the distal portion 115 of the body member 100), the pusher tube 105 is advanced a selected distance distally relative to the outer tube 30, thereby ejecting the distal-most tissue anchor 125b from the open distal tip 85 of the outer tube 30, with the proximal-most tissue anchor 125a remaining in the outer tube 30. Subsequently, e.g., after relocating the distal tip 85 of the outer tube 30 to another location on an opposite side of the aperture in the annulus fibrosus to be repaired, the pusher tube 105 can be advanced distally a second distance to eject the proximal-most tissue anchor 125a.

Thus, as can be seen in FIGS. 2A and 2B, the implant delivery tool 20 includes additional features for facilitating advancement of the plunger assembly 40 in discrete steps selectively and sequentially eject multiple tissue anchors in series from the outer tube 30. For example, the implant delivery tool 20 includes an axial spring 150 in the body 35 configured to bias the plunger assembly 40 in the proximal direction, and further includes a pin 155 biased radially inwardly by a lateral spring 160. The pin 155 is positioned to engage slots in the distal portion 115 of the plunger member 100 (described in further detail below) to control the distal movement of the plunger assembly 40 relative to the body 35 and the outer tube 30. These features are similar or identical to corresponding features illustrated and described with respect to the fixation delivery apparatus 400 of FIGS. 48A-48E of the aforementioned U.S. Patent Publication 2009/0259260, and thus need not be described in further detail here.

Figure 3:
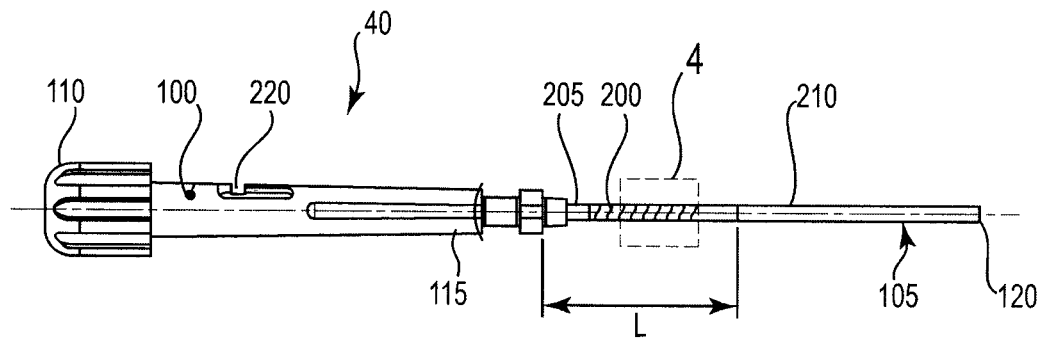
FIG. 3 is an elevation view of a plunger assembly of the implant delivery tool shown in FIG. 2, including a pusher tube according to one embodiment of the present invention.

FIG. 3 is an elevation view of the plunger assembly 40 of the implant delivery tool 20 according to one embodiment of the present invention. As shown in FIG. 3, the pusher tube 105 includes a flexible segment 200 disposed between substantially rigid proximal and distal segments 205, 210. As further shown, the proximal segment extends from the distal portion 115 of the plunger member 100, and the distal segment 210 extends distally from the flexible segment 200 and terminates in the distal end 120 of the pusher tube 105. In various other embodiments, the flexible segment 200 extends directly from the distal portion 115 of the plunger member 100, i.e., the rigid proximal segment 205 is omitted. In other embodiments, the relatively rigid proximal segment 205 is present and the relatively rigid distal segment 210 is omitted, and thus the flexible segment 200 extends from the proximal segment 205 to the distal end 120. In still other embodiments, the entire length of the pusher tube 105 is flexible, and thus the pusher tube 105 includes no rigid proximal or distal segments 205, 210.

As further shown, the distal portion 115 of the plunger member 100 includes one or more slots 220 shaped and positioned to be engaged by the pin 155 (see FIG. 2A) for controlling the advancement of the plunger assembly 40, as described above and in the aforementioned U.S. Patent Publication No. 2009/0259260, which is incorporated herein by reference in its entirety.

The flexible segment 200 is configured to have a relatively high degree of flexibility in response to laterally-applied forces (i.e., bending forces) without significantly reducing the column strength of the pusher tube 105. Additionally, the flexible segment 200 is positioned along the pusher tube 105 so that the intermediate section 65 of the pusher tube 30 (see, e.g., FIGS. 2A and 2B) is axially coincident with the flexible segment 200 through the entire range of displacement of the pusher tube 105 relative to the outer tube 30. That is, in various embodiments, the flexible segment 200 is dimensioned and positioned such that neither the rigid proximal segment 205 (if present) nor the rigid distal segment 210 of the pusher tube 105 will extend into the intermediate section 65 of the outer tube in any of the plurality of positions of pusher tube 105 relative to the outer tube 30. Accordingly, the flexible segment 200 has a predetermined length L which, in various embodiments, is selected to be greater than the overall length of the intermediate section 65 of the outer tube 30. Thus, the flexible segment 200 of the pusher tube will substantially conform to the curved or non-linear shape of the intermediate section 65 of the outer tube 30 throughout the entire range of positions of the pusher tube 105.

Overall, the pusher tube 105 has a generally cylindrical tubular structure, with the flexible segment 200 including features to impart the desired degree of flexibility without significantly affecting the column strength (i.e., resistance to buckling) of the pusher tube 200. In one embodiment, the pusher tube 105 has an outside diameter of about 0.042 inches and an inside diameter of about 0.035 inches. In other embodiments, the pusher tube 105 may have different inside and outside diameters depending on the particular therapeutic needs for the repair device 10.

While not shown in FIG. 2A-2C or FIG. 3, in various embodiments, the implant delivery tool 20 may include additional support features within the body 35, the outer tube 30, and/or the plunger assembly 40 to support portions of the flexible segment 200 of the pusher tube 105. For example, in one embodiment, the body 35 or the outer tube 30 can include a sleeve (not shown) which extends proximally into the body 35 and slidably receives the proximal portions of the flexible segment 200. In one embodiment, the distal portion 115 of the plunger member 100 can include a counterbore (also not shown) to receive the support sleeve on the outer tube 30 and/or the body 35 as the plunger member 100 and the pusher tube 105 are advanced distally relative to the body 35 and the outer tube 30.

Figure 4:
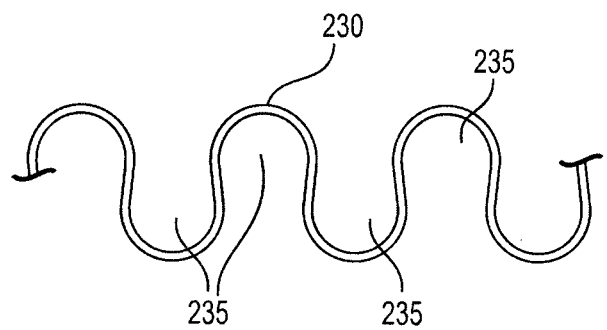
FIG. 4 is a schematic view illustrating a slot arrangement for imparting flexibility in a flexible segment of the pusher tube of FIG. 3 according to one embodiment of the present invention.

FIG. 4 is a schematic drawing illustrating one technique for imparting lateral flexibility to the flexible segment 200 of the pusher tube 105, according to one embodiment of the present invention. In the illustrated embodiment, the flexible segment 200 includes a slot 230 cut through the wall of the pusher tube 200 in a helical pattern around the circumference of the pusher tube 200. As shown, the slot 230 has an undulating shape defining a series of keys 235. The slot 230 is dimensioned to allow a degree of freedom to allow the flexible segment 200 to bend as the pusher tube 105 is advanced distally within the outer tube 30. In one embodiment, the slot 230 is configured to have an average of about five keys 235 per rotation about the pusher tube 105.

In other embodiments, other techniques can be employed to impart the desired flexibility in the flexible segment 200. For example, in various embodiments, the slot 230 can have any of a number of shapes providing the desired degree of freedom of movement in response to lateral (i.e., bending) forces. In one embodiment, the slot 230 does not have an undulating shape, and thus takes on the configuration of a helical spring (i.e., without defining any keys 235). In still other embodiments, the flexible segment 200 can be heat treated to impart flexibility therein in addition to or in lieu of inclusion of the slot 230. In short, any technique for imparting bending flexibility to the flexible segment 200 can be employed within the scope of the present invention.

While the plunger assembly 100 described above utilizes a tubular pusher tube 105, in various other embodiments, the pusher tube 105 is replaced by a solid (i.e., non-tubular) pusher member, which may be made of a metallic or polymeric material selected to provide the requisite flexibility and also sufficient column strength to avoid buckling.

Figure 5A:
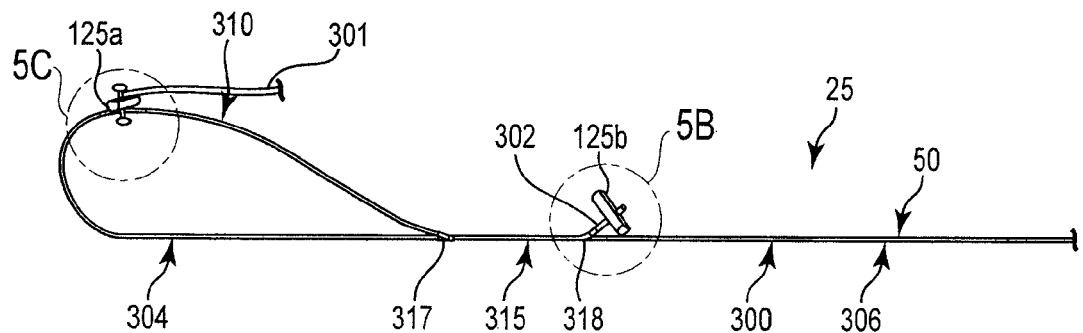
FIGS. 5A-5C are schematic views of an implant for use in the repair device of FIG. 1 according to one embodiment of the present invention.
Figure 5B:
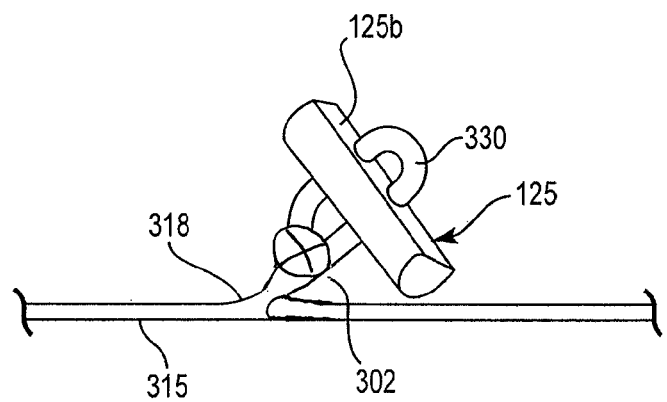
Figure 5C:
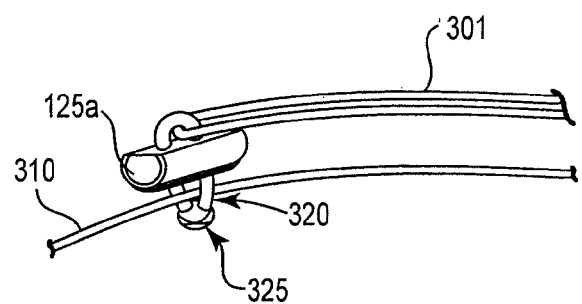

FIGS. 5A-5C are schematic views of the implant 25 for use in the repair device 10 of FIG. 1 according to one embodiment of the present invention. As shown, the implant 25 includes the tissue anchors 125a, 125b and adjustable flexible connecting element 300 connecting the tissue anchors 125a, 125b. As further shown, the implant 25 includes a retention line 301 coupled to the tissue anchor 125a. In various embodiments, the retention line 301 is provided to retain the tissue anchor 125a within the outer tube 30 of the implant delivery tool 20 during deployment of the distal tissue anchor 125b, to prevent undesired and premature ejection of the tissue anchor 125a from the outer tube 30.

In various embodiments, the retention line 301 extends proximally within the pusher tube 105 of the plunger assembly 40 or within the outer tube 30 and is connected to pusher tube 105, the plunger member 100, the body 35, or some other feature at the proximal end of the implant delivery tool 20. Once the tissue anchor 125a is deployed in the intervertebral disc tissue, the physician can cut and remove the retention line 301 from the implant 25. In other embodiments, the retention line 301 is configured to be automatically cut by and removed with the delivery tool 20 after deployment of the tissue anchor 125a, thus eliminating the need for a separate cutting step. In various other embodiments, the retention line 301 is omitted, and a different technique is employed to retain the tissue anchor 125a in the outer tube 30 prior to its intended deployment. For example, in one embodiment, the distal end 120 of the pusher tube 105 can include a hook or other feature to engage a knot or similar feature on the implant 25, and this engagement operates to retain the tissue anchor 125a in the outer tube 30. In still other embodiments, however, the functionality of the retention line 301 is omitted.

In the illustrated embodiment, the connecting element 300 is a knotless suture construct formed at least partially or wholly from a tubular, braided suture material and includes a distal segment 302, an intermediate segment 304 extending proximally from the distal segment 302, and a proximal segment 306 extending proximally from the intermediate segment 304 to form the tension line 50 (see FIG. 1).

As further shown, the intermediate segment 304 includes an adjustable loop 310 and a locking element 315 having a proximal end 317 and a distal end 318. As shown, the tissue anchor 125a is slidably coupled to the adjustable loop 310, and the tissue anchor 125b extends from the locking element 315, which is interposed between the tissue anchors 125a and 125b. As can be seen in FIG. 5C, the tissue anchor 125a is coupled to the adjustable loop 310 by a suture loop 320 extending through the tissue anchor 125a and secured thereto by a knot 325, thus allowing the tissue anchor 125a to slide along the length of the braided suture material of the adjustable loop 310. Additionally, the distal segment 302 extends through the tissue anchor 125b and is secured thereto by a locking arrangement 330, which in the illustrated embodiment is a knotted loop, and then extends proximally along a fixed length to the locking element 315. In various embodiments, the distal segment 302 may include only a single strand of suture material, and the locking element 330 is a knot, pledget, or similar structure which prevents the distal segment 302 from being pulled through and detached from the tissue anchor 125b.

In the illustrated embodiment, the connecting element 300 is formed by forming the adjustable loop 310 with the braided suture material of the intermediate segment 304, and then running the suture material back through an outer wall of a length of the braided suture material to form the locking element 315 in the form of a tubular braided catch. That is, a length of the intermediate segment 304 is inserted through the outer suture wall and into the interior of the braided suture material at the proximal end 317 of the locking element 315, then exits the braided suture material at the distal end 318 of the locking element 315, and thereafter extends proximally to form the proximal segment 306 and the tension line 50.

In this configuration, when tension is applied between the tension line 50 and the tissue anchor 125a and/or 125b, the overall length of the adjustable loop 310 is reduced thus reducing the separation between the tissue anchors 125a and 125b. As can be seen from FIGS. 5A and 5C, as the length of the adjustable loop 310 is reduced, the suture loop 320 allows the tissue anchor 125a to slide along the adjustable loop 310. The braided locking element 315 radially constricts the portion of the intermediate segment 304 extending internally therein, operating to prevent reverse movement of the suture material of the intermediate segment 304 extending within the locking element 315. Thus, once the adjustable loop 310 is shortened, the locking element 315 will prevent subsequent elongation of the adjustable loop 310.

In the illustrated embodiment, the adjustable connecting element 300 is formed from a single, continuous length of braided suture material. However, in other embodiments, the connecting element 300 is formed from different materials coupled together to form the various components of thereof. For example, in one embodiment, the locking element 315 is a separate braided tube disposed over the suture material forming the other components of the connecting element 300.

Thus, in use, the tissue anchor 125b is first ejected from the outer tube 30 of the implant delivery tool 20 and into or through the annulus fibrosus, as discussed above. Subsequently, the outer tube 30 is removed from the annulus fibrosus and re-inserted at a different location (e.g., on an opposite side of the aperture to be repaired) and the tissue anchor 125a is then ejected into the annulus fibrosus. As explained above, the retention line 301, if present, operates to retain the tissue anchor 125a in the outer tube 30 during deployment of the tissue anchor 125b and subsequent repositioning of the implant delivery tool 20. After deployment of the tissue anchor 125a, the retention line 301 can be wholly or partially removed, e.g., by cutting the retention line proximate the tissue anchor 125a.

The physician can then apply tension to the tension line 50, which will be resisted by the tissue anchor 125a and/or 125b bearing against the annulus fibrosus tissue. With the tissue anchors 125a, 125b effectively secured in place against the annulus fibrosus, the tension line 50 can be pulled through the locking element 315 to shorten the length of the adjustable loop 310 between the tissue anchors 125a, 125b. In this way, once both tissue anchors 125a and 125b bear against the annulus fibrosus tissue, the tissues defining the aperture can be pulled toward one another under tension by further reducing the length of the adjustable loop between the tissue anchors 125a, 125b, thereby at least partially or wholly closing the aperture. The design of the locking element 315, as discussed above, substantially prevents subsequent reverse movement of the tension line through the locking element 315, thus maintaining the adjustable loop 310 in tension between the tissue anchors 125a and 125b. Any excess length of the tension line 50 can subsequently be cut away to complete the implantation procedure.

Figure 6A:
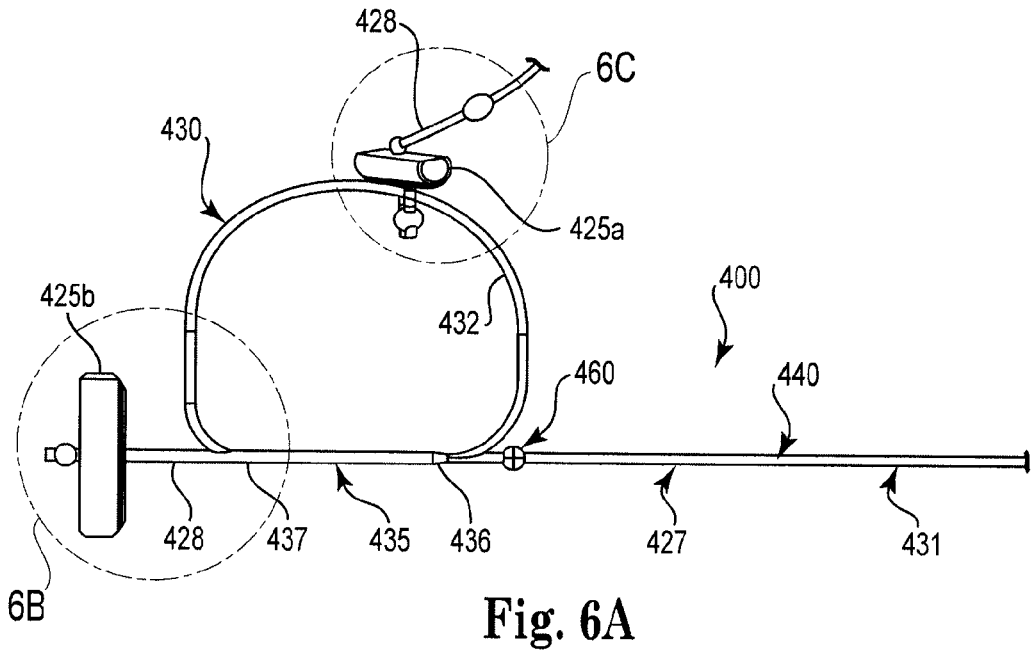
FIGS. 6A-6C are schematic views of an alternative implant for use in the repair device of FIG. 1 according to one embodiment of the present invention.
Figure 6B:
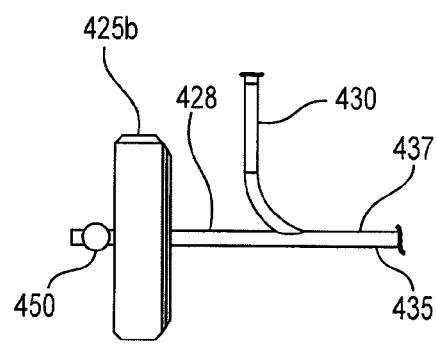
Figure 6C:
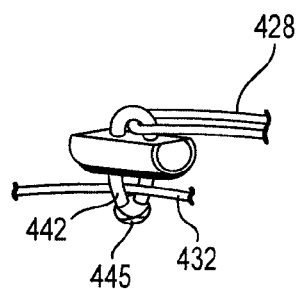

FIGS. 6A-6C are schematic views of an alternative implant 400 for use in the repair device 10 according to one embodiment of the present invention. As shown in FIGS. 6A-6C, the implant 400 includes a pair of tissue anchors 425a, 425b, an adjustable flexible connecting element 427 connecting the tissue anchors 425a, 425b, and a retention line 428. In the illustrated embodiment, the connecting element 427 is a knotless suture construct formed at least partially or wholly from a tubular, braided suture material and includes a distal segment 428, an intermediate segment 430 and a proximal segment 431.

As further shown, the intermediate segment 430 includes an adjustable loop 432, a locking element 435 having a proximal end 436 and a distal end 437, and the proximal segment 431 forms a tension line 440. The retention line 428, the locking element 435 and the tension line 440 may, in various embodiments, be configured in substantially the same manner as the retention line 301, the locking element 315 and the tension line 50 described above with respect to the implant 25, and are thus not described in further detail again here.

As shown, the tissue anchor 425a is slidably coupled to the adjustable loop 432, and the tissue anchor 425b is fixedly connected to the locking element 435, which is interposed between the tissue anchors 425a and 425b. As can be seen in FIG. 6C, the tissue anchor 425a is coupled to the adjustable loop 430 by a suture loop 442 extending through the tissue anchor 425a and secured thereto by a knot 445. Additionally, the tissue anchor 425b is fixedly attached to the distal segment 428 by a knot 450, and the distal segment 428 extends proximally along a fixed length to the locking element 435.

In the illustrated embodiment, the connecting element 427 is formed by forming the adjustable loop 432 with the braided suture material of the intermediate segment 430, and then running the suture material back through an outer wall of the braided suture material to form the locking element 435 in the form of a tubular braided catch. That is, a length of the intermediate segment 430 is inserted through the outer suture wall and into the interior of the braided suture material at the distal end 437 of the locking element 435, and then exits the braided suture material at the proximal end 436 of the locking element 435, thereafter extending proximally to form the proximal segment 431 and the tension line 440. In this configuration, when tension is applied between the tension line 440 and the tissue anchor 425b, the overall length of the adjustable loop 432 is reduced thus reducing the separation between the tissue anchors 425a and 425b. As can be seen from FIGS. 6A and 6C, as the length of the adjustable loop 432 is reduced, the suture loop 442 allows the tissue anchor 425a to slide along the adjustable loop 432. However, once the adjustable loop 432 is shortened, the locking element 435 will prevent subsequent elongation of the adjustable loop 432.

Prior to deployment, the tissue anchor 425a is disposed within the outer tube 30 of the implant delivery tool 20 proximal to the tissue anchor 425b. In the illustrated embodiment, the connecting element 427 further includes a resistance feature 460 on the tension line 440 proximal to the locking element 435, which is positioned inside the outer tube 30 prior to and during deployment of the tissue anchors 425a, 425b to encourage toggling/rotation of the tissue anchors 425a, 425b as they are ejected from the outer tube 30. In the illustrated embodiment, the resistance feature 460 is in the form of a knot dimensioned to contact the inner surface of the outer tube 30. In various other embodiments, the resistance feature can take on a different form (e.g., a resilient sphere or cylinder disposed over the connecting element 427 suture material), or may be eliminated altogether.

In use, the implant 400 operates in much the same manner as the implant 25 described above. That is, the tissue anchor 425b is first ejected from the outer tube 30 of the implant delivery tool 20 and into or through the annulus fibrosus, as discussed above. Subsequently, the outer tube 30 is removed from the annulus fibrosus and re-inserted at a different location (e.g., on an opposite side of the aperture to be repaired) and the tissue anchor 425a is then ejected into the annulus fibrosus. The retention line 428, if present, operates to retain the tissue anchor 425a in the outer tube 30 during deployment of the tissue anchor 425b and repositioning of the implant delivery instrument 20. The physician can then apply tension to the tension line 440, which will be resisted by the tissue anchor 425a and/or 425b bearing against the annulus fibrosus tissue. With the tissue anchors 425a, 425b effectively secured in place against the annulus fibrosus, the tension line 440 can be pulled through the locking element 435 to shorten the length of the adjustable loop 432 between the tissue anchors 425a, 425b. In this way, once both tissue anchors 425a and 425b bear against the annulus fibrosus tissue, the tissues defining the aperture can be pulled toward one another under tension by further reducing the length of the adjustable loop between the tissue anchors 425a, 425b, thereby at least partially or wholly closing the aperture. The design of the locking element 435, as discussed above, substantially prevents subsequent reverse movement of the tension line through the locking element 435, thus maintaining the adjustable loop 430 in tension between the tissue anchors 425a and 425b. Any excess length of the tension line 440 can subsequently be cut away to complete the implantation procedure.

Although the implants 25, 400 described above include knotless connecting elements 300, 427, this is not a requirement. Thus, in various embodiments, the knotless locking elements of the respective implants can be replaced by knots, e.g., Roeder knots, Weston knots, or similar constructs, by pledgets, or by other structures allowing for shortening the length of the connecting element portion between the tissue anchors while resisting or preventing subsequent elongation thereof. In sort, any technique for providing the requisite length adjustment capability in the connecting elements 300, 427 can be employed within the scope of the present invention.

In various embodiments, two repair devices 10 can be provided, e.g., as in an annulus fibrosus repair system, for deployment of two implants 25 or 400 to effectuate re-approximation of an aperture in the annulus fibrosus. In one embodiment, the two implants 25 or 400 can be deployed in a manner such that the portions of the respective adjustable connecting elements spanning across the aperture external to the outside surface of the annulus fibrosus cross each other, in the form of an "X." This construct advantageously provides multi-location contact between the respective tissue anchors and connecting elements to effectively draw together the tissues defining the aperture in the annulus fibrosus.

In still other embodiments, the repair device 10 can be used to secure another implant, e.g., an occlusion device, to an implantation within the annulus fibrosus to occlude an aperture therein. This can be in addition to or in lieu of partially or wholly closing the aperture itself using the repair device 10. For example, in one embodiment, an expandable occlusion device can be implanted within the intervertebral disc so as to span across the aperture in the annulus fibrosus, and one or more implants 25, 400 can then be implanted into or through both the annulus fibrosus tissue and the occlusion device to secure the occlusion device in place. Exemplary occlusion devices that can be used in this manner are described and illustrated in co-pending and commonly assigned U.S. Patent Publication No. 2005/0283246, the disclosure of which is incorporated herein by reference. In other embodiments, a patching element can be positioned on the exterior surface of the annulus fibrosus and secured in place using the implants 25 and/or 400.

While the tissue anchors 125a/b and 425a/b illustrated above are shown and described as T-anchors, in various embodiments, these tissue anchors can take on any number of forms providing the desired degree of tissue contact and engagement with the annulus fibrosus. In various embodiments, the tissue anchors 125a/b and/or 424a/b can be constructed to be configured such as the T-anchors 815 shown in FIG. 69 and/or the T-anchors 951a/b in FIGS. 70, 71A-B, 72 and 73 of the aforementioned co-pending and commonly assigned U.S. Patent Publication 2009/0259260, which is incorporated herein by reference in its entirety.

The materials used in the implant delivery tool 20 or the implants 25, 400 can include any number of biocompatible materials having suitable mechanical properties. Materials of which to make the outer tube 30 and/or the push tube 105 of the implant delivery tool 20 and also the tissue anchors 125a/b and/or 435a/b of the implants 25, 400 can include, but are not limited to: metals, such as stainless steel, nickel, titanium alloy, and titanium; plastics, such as polytetrafluoroethylene (PTFE), polypropylene, polyether etherketone (PEEK™), polyethylene, polyethylene teraphthalate (PET) and polyurethane, acrylic, polycarbonate, engineering plastics; and/or composites. The adjustable connecting elements 300, 427 can likewise be made of any suitable suture material. In various embodiments, the connecting elements 300, 427 are made wholly or partially of size 2-0 or 3-0 force fiber suture material. In short, any suitable materials, whether now known or later developed, can be utilized to construct the implant delivery tool 20 and the implants 25, 400, within the scope of the present invention.

Figure 7:
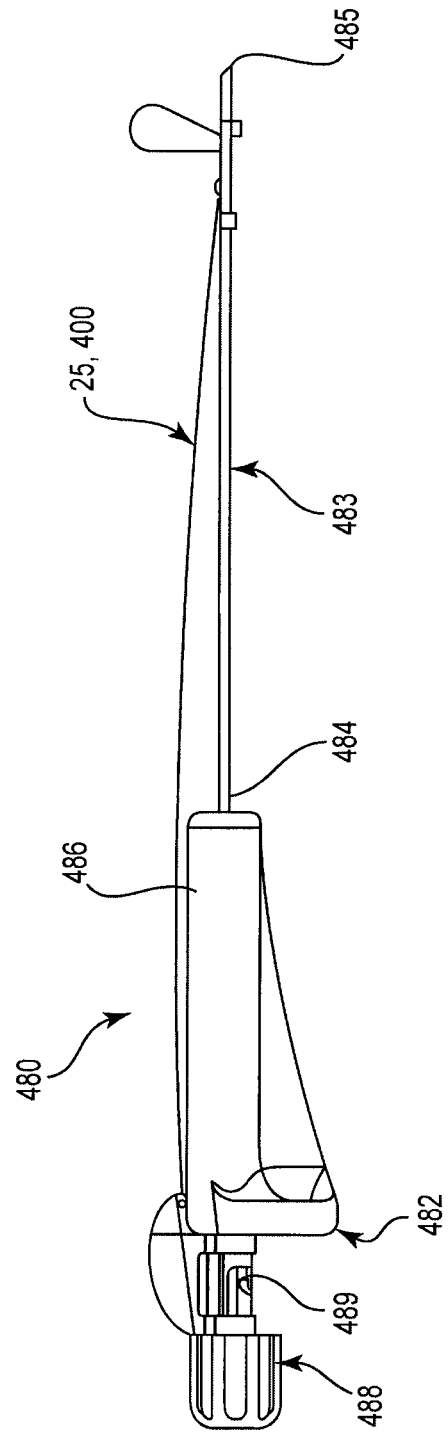
FIG. 7 is a schematic illustration of an alternative device for use in repairing an aperture or a defect in an annulus fibrosus of an intervertebral disc using the implants of FIGS. 5A-5C and 6A-6C according to another embodiment of the present invention.

FIG. 7 illustrates an alternative device 480 for use in repairing an aperture or a defect in an annulus fibrosus of an intervertebral disc utilizing the implants 25, 400 according to an embodiment of the present invention. The device 480 includes an implant delivery tool 482 and an implant 25 or 4000 as described above. The implant delivery tool 482 is, except as noted below, substantially the same or identical in structure and function to the implant delivery tool 20 described above. Accordingly, as shown in FIG. 7, the implant delivery tool 482 and includes an a substantially rigid outer tube 483 having a proximal section 484 and a sharpened distal tip 485, a body 486 coupled to the proximal section 484 of the outer tube 483, and a plunger assembly 488 movable axially relative to the body 486. The plunger assembly 488 also includes plunger member 489 and a pusher tube (not shown in FIG. 7 coupled thereto and disposed within the outer tube 483. The implant delivery tool 482 differs from the implant delivery tool 20 in that the rigid outer tube 483 is generally straight, and does not include the offset intermediate section of the outer tube 30 of the implant delivery tool 20. Accordingly, in various embodiments, the implant delivery tool 482 is functionally and structurally similar to the fixation delivery apparatus 400 of FIGS. 48A-48E of the aforementioned U.S. Patent Publication 2009/0259260, which is incorporated herein by reference in its entirety.

Figure 8A:
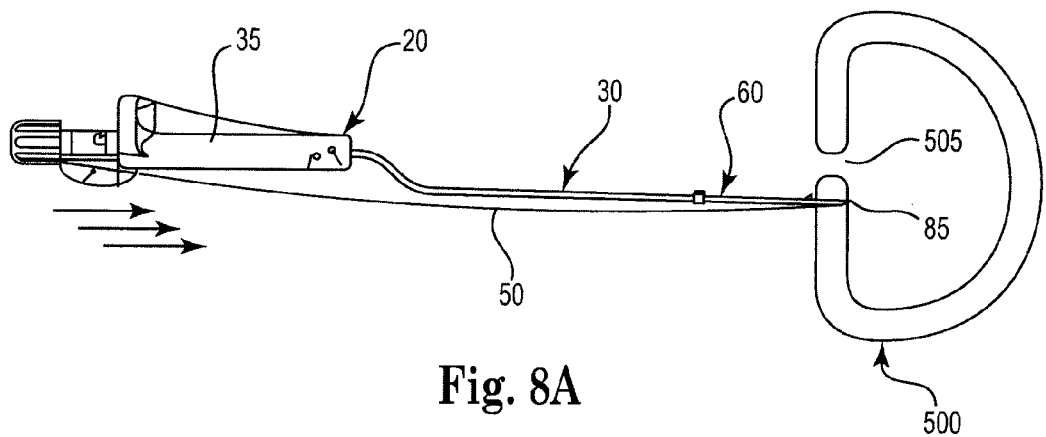
FIGS. 8A-8C are schematic illustrations showing the annulus fibrosus repair device of FIG. 1 in use during a repair procedure on an annulus fibrosus.
Figure 8B:
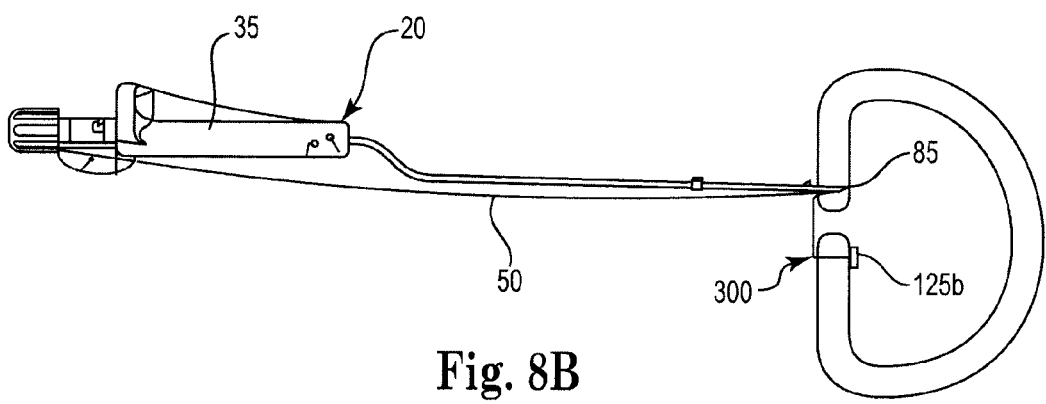
Figure 8C:
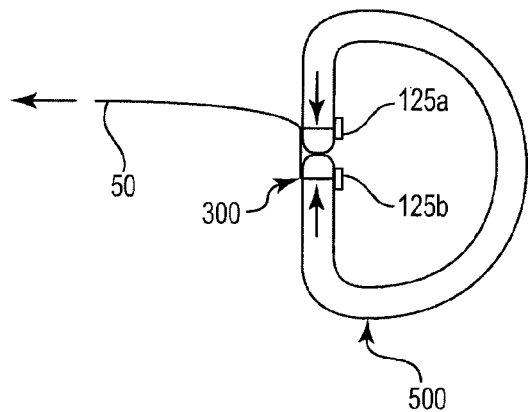

FIGS. 8A-8C are schematic illustrations showing the annulus fibrosus repair device 10 of FIG. 1 in use during a repair procedure on an annulus fibrosus 500, and in particular, a procedure to re-approximate tissues defining an aperture 505 in the annulus fibrosus 500. As shown in FIG. 8A, in use, the distal section 60 of the outer tube 30 of the implant delivery tool 20 is partially inserted into or through the annulus fibrosus 500 near the aperture 505 for deploying the tissue anchor 125b (not shown in FIG. 8A) from the distal tip 85 of the outer tube 30. As further illustrated, because the offset in the outer tube 30 maintains a clear line of site to the implantation location, without visual interference by the body 35 of the implant delivery tool 20, and consequently, the physician's own hands.

As can be seen in FIG. 8B, after deployment of the tissue anchor 125b, the implant delivery tool 20 is subsequently removed and reinserted into or through the tissue of the annulus fibrosus 500 at a second location on the opposite side of the aperture 505. As shown, a portion of the adjustable connecting element 300 extends across the aperture 505 external to the outer surface of the annulus fibrosus. Again, as can be seen in FIGS. 8A and 8B, during insertion of the distal tip 85 of the outer tube 30 of the implant delivery tool 20 into the annulus fibrosus 500 proximate the aperture 505, the offset configuration of the outer tube 30 results in the body 35 of the implant delivery tool 20 being removed from physician's line of sight to the repair site.

Subsequently, as shown in FIG. 8C, after deployment of the tissue anchor 125a and removal of the implant delivery tool 20 from the tissue of the annulus fibrosus 500, the tension line 50 is pulled to shorten the length of the adjustable connecting element 300 between the tissue anchors 125a, 125b, thereby pulling together and re-approximating the tissues defining the aperture 500. While not shown in FIG. 8C, excess length of the tension line 50 can then be removed.

In various embodiments, multiple devices 10 each including an implant delivery tool 20 and an implant 25 or 400 can be utilized as a system for intervertebral disc annulus repair. For example, in various embodiments, after deploying the first implant 25 and at least partially re-approximating tissues defining the aperture 500 as shown in FIG. 8C, a second device 10 can be utilized to deploy a second implant 25 to further re-approximate the defect and/or to augment or reinforce the previously implanted implant 25. In such embodiments, the second implant 25 may be deployed using the same or similar techniques illustrated in FIGS. 8A-8C, with each tissue anchor 125a, 125b of the second implant 25 being inserted into the annulus at different locations such that the adjustable connecting element 300 spans across the defect. The length of the adjustable connecting element 300 of the second implant 25 can then be shortened to complete the re-approximation procedure. Of course, the implant 400 could be utilized in place of the implant 25 in any of the foregoing procedures.

FIGS. 9A-9C are plan and cut-away elevation views of an implant delivery tool 600 with an implant 610 coupled thereto according to another embodiment of the present invention. As shown in FIGS. 9A-9C, the delivery tool 600 includes a body 612 including a proximal handle 616 and an outer tubular member 620 extending distally from the handle 616 and having an open distal end 624. As further shown, the delivery tool 600 has a needle cannula 628, a pusher member 634, and an actuating mechanism 640. In the illustrated embodiment, the needle cannula 628 is slidably received within the outer tubular member 620, and the pusher member 634 is slidably received within the needle cannula 628. Additionally, the actuating mechanism 640 includes a lever 646 pivotally coupled to the handle 616, and a releasable safety tab 648 is connected to a portion of the implant 610 and to the inner pusher member 634. As will be explained and illustrated in further detail below, the lever 646 is configured to engage the needle cannula 628 for selectively adjusting the axial position of the needle cannula 628 relative to the pusher member 634 and the outer tubular member 620. In addition, the safety tab 648 is coupled to the pusher member 634 and is operable to prevent unintended, spontaneous axial movement of the needle cannula 628 and the pusher member 634 relative to the outer tubular member 620, as well as to assist the clinician in deploying the implant 610.

As further shown, in the pre-deployed state of FIGS. 9A-9C, the implant 610 is disposed within the needle cannula 628 and includes an anchor member 650 and an adjustable suture assembly 654. In the illustrated embodiment, the adjustable suture assembly 654 is connected to the anchor member 650 and also to the delivery tool 600, as will be explained in further detail below. In various embodiments, the anchor member 650 is configured to be implanted within a vertebra or soft tissue of the patient's spine, and the adjustable suture assembly 654 is configured to be interconnected to a second implant and placed under tension so as to repair a defect or aperture in the annulus fibrosus. Thus, the implant 610 can, in various embodiments, be used to re-approximate an aperture in the annulus fibrosus in the same manner as the systems disclosed in co-pending and commonly assigned U.S. application Ser. Nos. 12/251,295 and 12/553,583, the entire disclosures of which are incorporated herein by reference in their entireties.

The delivery tool 600 is configured to be operated by a clinician to deploy the anchor member 650 into the vertebra and to facilitate tensioning the adjustable suture assembly 654 for repairing the anular defect. In various embodiments, the delivery tool 600 is configured such that, prior to deployment of the anchor member 650, the needle cannula 628 and the pusher member 634 are disposed within the outer tubular member 620, as is shown in FIG. 9A. Additionally, the needle cannula 628 and the pusher member 634 can be advanced distally together relative to the outer tubular member 620, e.g., to penetrate a vertebral body with the tip of the needle cannula 628 for insertion of the anchor member 650 into the vertebral body, and the needle cannula 628 can subsequently be retracted proximally while the pusher member 634 remains stationary, thereby releasing the anchor member 650 from the needle cannula 628 into the vertebra. The delivery tool 600 advantageously facilitates deployment of the anchor member 650 into the vertebra without requiring first drilling or otherwise forming a hole in the vertebra (e.g., with a bone awl) to receive the anchor member 650.

Figure 10A:
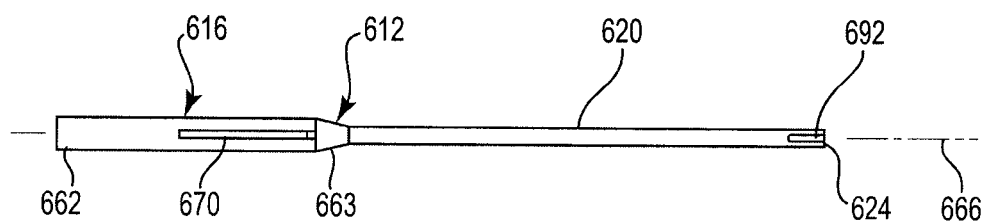
FIGS. 10A-10C are plan and cross-sectional elevation views of a handle and outer tubular member of the delivery tool of FIGS. 9A-9C according to one embodiment of the present invention.
Figure 10B:
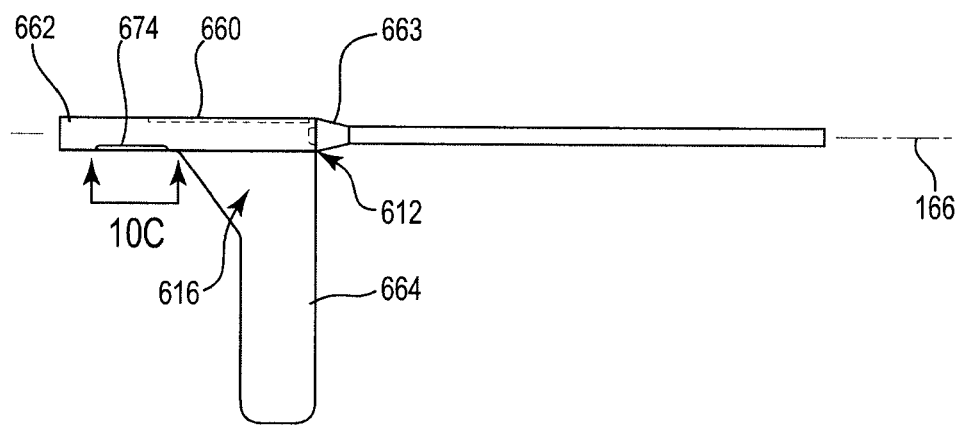
Figure 10C:
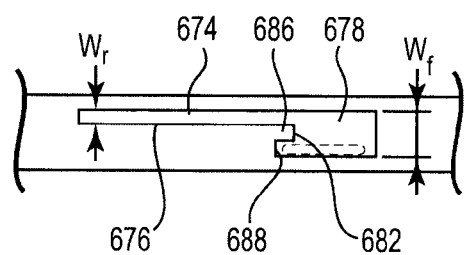

FIGS. 10A-10C are plan and cross-sectional elevation views of the body 612 of the delivery tool 600 according to one embodiment of the present invention. As shown in FIGS. 10A-10C, the handle 616 includes a tubular upper portion 660 having a proximal end 662 and a distal end 663, and a lower portion 664 extending from the upper portion 660. As further shown, the outer tubular member 620 extends distally from the distal end 663 of the handle upper portion 660, and the handle upper portion 660 is generally aligned with the tubular outer member 620 of the delivery tool 600 so as to define a longitudinal axis 666 of the delivery tool 600. The lower portion 664 of the handle is adapted to be gripped by the clinician during use of the delivery tool 600. In the illustrated embodiment, the lower portion 664 extends generally orthogonal to the upper portion 660 and the longitudinal axis 666, although in other embodiments, the lower portion 664 may extend from the upper portion 660 at an oblique angle.

As further shown, in FIG. 10C, the upper portion 660 of the handle 616 includes an upper slot 670 and a lower slot 674 disposed generally 180 degrees from the upper slot 670. In the illustrated embodiment, the upper and lower slots 670, 674 are located between the proximal and distal ends 662, 663. Additionally, the upper slot 670 has a generally constant width along its length. In contrast, in the illustrated embodiment, the lower slot 674 has a rear segment 676 having a first width Wr (see FIG. 10C) and a forward segment 678 having second width Wf (see FIG. 10C). In the illustrated embodiment, Wf is greater than Wr so as to define a shoulder 182 at the transition between the rear and forward segments 676, 678. Additionally, as further shown, a projection 686 extends distally from the shoulder 682, forming a recess 688.

As will be explained in further detail below, upper and lower slots 670, 674 are dimensioned and configured to slidingly receive and guide structures on the needle cannula 628 and pusher member 634, respectively. Additionally, the recess 688 is sized to receive a structure (shown in dashed lines in FIG. 10C) on the inner pusher member 634 such that the projection 686 operates as a rotation stop preventing unintentional rotation of the pusher member 634.

As further shown, in the illustrated embodiment, the outer tubular member 620 includes a slot 692 extending proximally from the open distal end 624. The slot 692 provides means by which portions of the adjustable suture assembly 654 can extend from within the needle cannula 628 (see FIG. 9C).

Figure 11A:
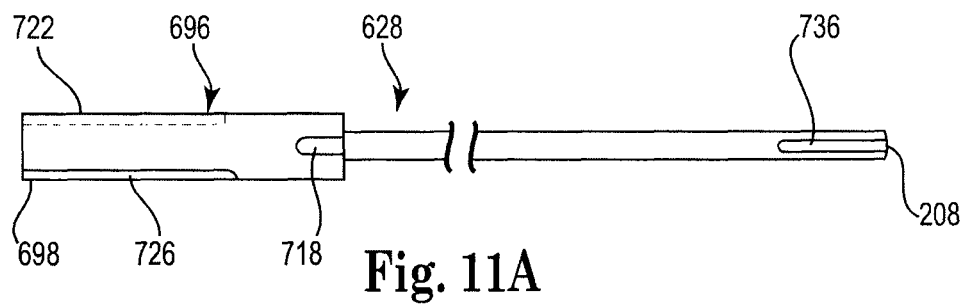
FIGS. 11A-11C are top, elevation and end views of a needle cannula of the delivery tool of FIGS. 9A-9C according to one embodiment of the present invention.
Figure 11B:
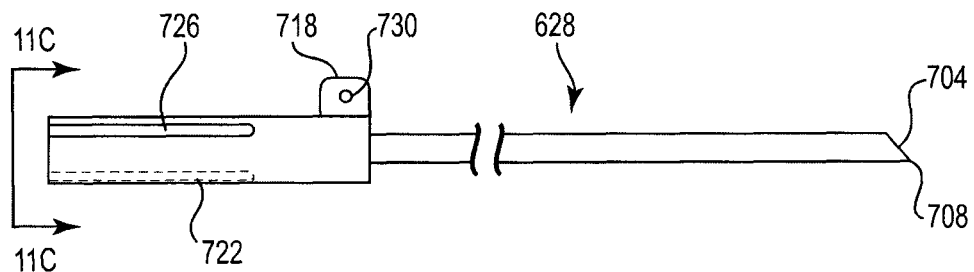
Figure 11C:
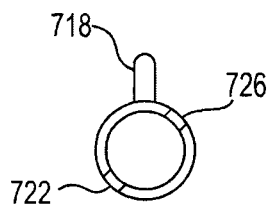

FIGS. 11A-11C are plan and elevation views of the needle cannula 628 of the delivery tool 610 according to one embodiment of the present invention. As shown, the needle cannula 628 has a proximal portion 696 with a proximal end 698, and an open distal end 704 terminating in a sharpened distal tip 708. In the illustrated embodiment, the proximal portion 696 includes a flange 718 and a pair of diametrically disposed slots 722, 726 extending distally from the proximal end 698. In the illustrated embodiment, the flange 718 includes an aperture 730 for attaching a portion of the adjustable suture assembly 654 of the implant 610, as explained further below. The needle cannula 628 is dimensioned to be slidingly received within the outer tubular member 620, and the flange 718 is dimensioned to be slidingly received within the upper slot 670 in the upper portion 660 of the handle 616. Thus, when assembled, the flange 718 extends from and slides axially within the upper slot 670, which further operates to prevent rotation of the needle cannula 628.

In the illustrated embodiment the proximal portion 696 of the needle cannula 628 includes sleeve structure fixedly attached to a tubular needle. In various other embodiments, the needle cannula 628 can be configured to include the flange 718 and slots 722, 726 as integral features of the tubular needle.

As shown, the slots 722, 726 are radially offset from the flange 718. The slots 722, 726 have widths selected to slidingly receive structures on the pusher member 634 to allow relative axial movement but prevent relative rotation of the needle cannula 628 and the pusher member 634 when aligned. At the same time, the proximal portion 696 is configured to engage structures on the pusher member 634 when not aligned so as to prevent relative axial movement of the needle cannula 628 and the pusher member 634.

As further shown, the needle cannula 628 further includes a slot 736 adjacent to the open distal end 704. In the illustrated embodiment, the slot 736 is radially aligned with the flange 718, and when assembled with the handle 616 and the outer tubular member 620, with the slot 692 in the outer tubular member 620. Thus, the slots 692 and 736 both operate to allow portions of the implant adjustable suture assembly 654 to extend from the needle cannula 628.

Figure 12:
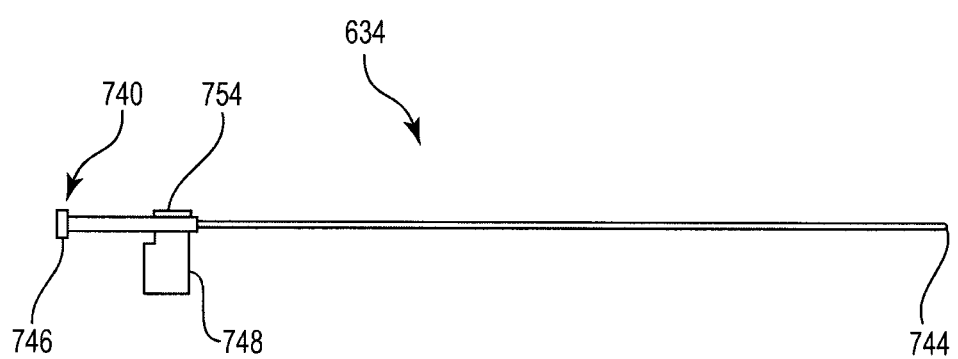
FIG. 12 is an elevation view of a pusher tube of the delivery tool of FIGS. 9A-9C according to one embodiment of the present invention.

FIG. 12 is an elevation view of the pusher member 634 of the delivery tool 600 according to one embodiment of the present invention. As shown in FIG. 12, the pusher member 634 has a proximal end 740 and a blunt distal end 744. As further shown, at the proximal end 740 is an end plate 746. The pusher member 634 further includes a radially extending tab 748, and a radially extending projection 754 disposed diametrically opposite the tab 748. When assembled, the pusher member 634 and the needle cannula 628 are configured so that the tab 748 and the projection 754 engage the proximal portion 696 of the needle cannula 628 when not aligned with the slots 722, 726, thereby preventing axial movement of the pusher member 634 relative to the needle cannula 628. In turn, when the tab 748 and the projection 754 of the pusher member 634 are aligned with the slots 722, 726, the needle cannula 628 can be retracted axially relative to the pusher member 634, which facilitates deployment of the anchor member 650 into the patient's vertebra.

Additionally, the handle 616, the needle cannula 628 and the pusher member 634 are further configured such that, when assembled, the tab 748 can be received within the recess 688 in the upper portion 660 of the handle 616(see FIG. 10C), and at the same time aligned with the slot 726 in the needle cannula proximal portion 696. In this configuration, the projection 686 of the handle upper portion 660 prevents rotation of the pusher member 634 to maintain alignment of the tab 748 and the slot 726 during retraction of the needle cannula 628.

As further shown in FIG. 12, the end plate 746 extends radially relative to the pusher member 634. The end plate 746 facilitates driving the needle cannula 628 and the pusher member 634 disposed therein into the patient's vertebra (e.g., providing a bearing surface that can be tapped using a mallet).

The needle cannula 628 and the pusher member 634 are each dimensioned such that they can extend distally a desired distance (e.g., based on the desired depth of deployment of the anchor member 650 into the vertebra) beyond the distal end 624 of the outer tubular member 620 when fully advanced. Additionally, the pusher member 634 as a whole is longer than the needle cannula 628 (including the proximal portion 696), such that the distal end 744 of the pusher member 634 extends distally beyond both the distal end 704 of the needle cannula 628 and the distal end 624 of the outer tubular member 620 when the needle cannula 628 is retracted proximally relative to the pusher member 634.

Figure 13:
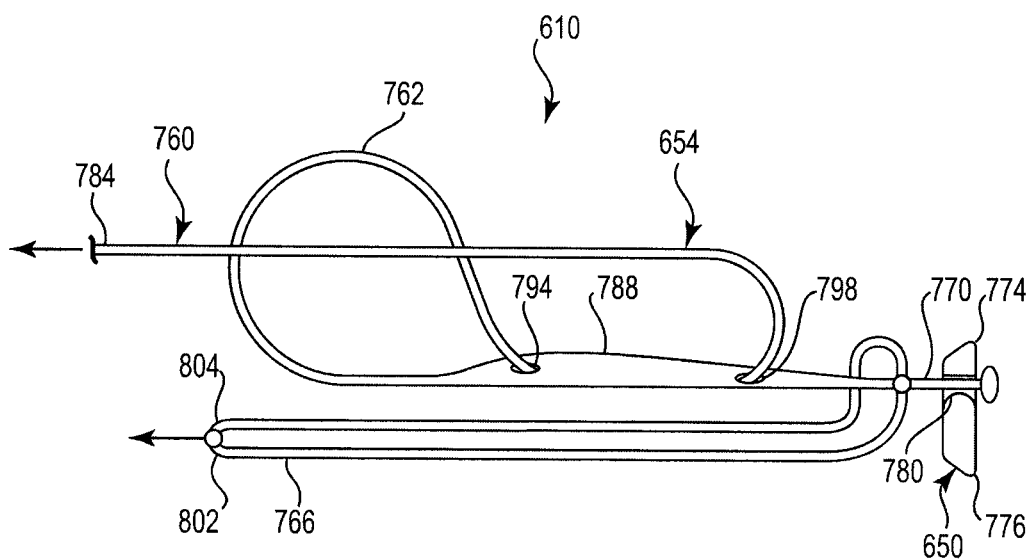
FIG. 13 is a schematic illustration of the implant of FIGS. 9A-9C according to one embodiment of the present invention.

FIG. 13 is a schematic illustration of the implant 610 showing details of the anchor member 650 and the adjustable suture assembly 654 according to one embodiment of the present invention. As shown in FIG. 13, the suture assembly 654 includes a tension line 760 forming a loop 762, a toggle line 766 and a connecting segment 770. As further shown, the anchor member 650 has opposed beveled ends 774, 776 and a channel 780 extending through the anchor member 650 generally orthogonally to the major length of the anchor member 650. In the illustrated embodiment, the channel 780 is located nearer to the beveled end 774 than the beveled end 776 which, as explained further below, facilitates toggling of the anchor member 650 during deployment to promote good engagement with the bone (e.g., vertebra) or other tissue in which the anchor member 650 is implanted.

As shown in FIG. 13, the connecting segment 770 extends through the channel 780 and is fixedly connected to the anchor member 650. As further shown, the tension line 760 extends from the connecting segment 280 and has a free end 284 and a locking element 288 which itself has first and second ends 294, 298. As shown, the locking element 288 is located between the free end 284 and the adjustable loop 762. In the illustrated embodiment, the tension line 760 including the locking element 288 is a knotless suture construct formed at least wholly or partially from a tubular, braided suture material to facilitate selective adjustment of the overall dimensions of the loop 762. Thus, as shown, the suture material of the tension line 262 enters the interior of the tubular suture material at the first end 294 of the locking element 288 and exits the interior of the tubular suture material at the second end 298 of the locking element 288, thereafter extending to the free end 284. As explained in further detail below, the free end 284 is connected to the safety tab 648 of the delivery tool 600, and can be manipulated by the clinician to reduce the dimensions of the loop 762 during an annular repair procedure.

In use, when tension is applied to the tension line 760 while the anchor member 650 is embedded in the patient's vertebra (or other tissue), the overall dimensions of the adjustable loop 762 are reduced. The braided locking element 288 allows the tension line 760 to move within the locking element 288 in the direction of the tensile force, while at the same time radially constricts the portion of the tension line 760 extending internally therein to prevent reverse movement of the tension line 760. Thus, once the dimensions of the adjustable loop 762 are reduced, the locking element 288 will prevent subsequent enlargement of the adjustable loop 288. Thus, the tension loop 260 is in many respects similar or identical to the knotless suture construct of the implants 25, 400 described above. In other embodiments, however, the tension line 760 with locking element 288 is not a knotless construct, but instead utilizes a knot (e.g., a Roeder knot or a Weston knot) or other means to facilitate one-way adjustment of the dimensions of the loop 762.

As further shown in FIG. 13, the toggle line 766 is attached to the connecting segment 770 and has ends 302, 304 which, as explained in further detail below, are tied together and connected to the flange 718 of the needle cannula 628 (see FIG. 9A). In one embodiment, the toggle line 766 is attached to the connecting segment 770 by one or more knots or other means to prevent sliding movement of the toggle line 766 relative to the connecting segment 770. Thus, tension applied to the toggle line 766 during operation of the delivery tool 600 is transferred directly to the connecting segment 770. In this way, because the connecting segment 770 is not centered on the anchor member 650 (due to the fact that the channel 780 is offset from the center of the anchor member), the anchor member 650 will tend to rotate when tension is applied to the toggle line 766, thus promoting engagement of the anchor member 650 to the bone or tissue in which it is implanted. In one embodiment, the toggle line 766 is configured to have a pre-determined breaking point, e.g., near the location at which it is attached to the connecting segment 770, such that the toggle line 766 will automatically break during actuation of the delivery tool 600. In such embodiments, the need to separately cut away the toggle line 766 after deployment of the anchor member 650 is avoided.

In other embodiments, however, the toggle line 766 is not designed to automatically break during actuation of the delivery tool 600. For example, in various embodiments, the toggle line 766 remains attached to the connecting segment 770 (or other component of the suture assembly 654) after complete deployment of the anchor member 650. In such embodiments, the toggle line 766 can be used by the clinician to ensure positive engagement of the anchor member 650 to the bone or other tissue in which it is deployed, e.g., by pulling on the toggle line 766 after deployment of the anchor member 650. In these embodiments, the toggle line 766 can thereafter be separately be cut away from the suture assembly 654.

Returning to FIGS. 9A-9C, in the assembled and pre-deployed configuration, the needle cannula 628 is disposed within the outer tubular member 620, and the proximal portion 696 being disposed within the upper portion 660 of the handle 616 with the flange 718 of the proximal portion 696 disposed in and extending outward from the upper slot 670. As further shown, the pusher member 634 is partially disposed within the needle cannula 628 and the upper portion 660 of the handle 616, with the proximal end 740, including the end plate 746, of the pusher member 634 extending proximally from the proximal end 662 of the handle upper portion 660. Additionally, the needle cannula 628 and the pusher member 634 are generally aligned with the longitudinal axis 166.

In the pre-deployed configuration shown, the tab 748 of the pusher member 634 is positioned in the rear segment 676 of the lower slot 674 in the handle upper portion 660. As explained above, the width Wr of the rear slot segment 676 is selected to substantially prevent rotation of the pusher member 634 relative to the handle 616 when so positioned. As further shown, the tab 748 and the projection 754 of the pusher member 634 are not radially aligned with the slots 722, 726 of the needle cannula proximal portion 696, but rather, abut and bear against the proximal portion 696. Accordingly, in this configuration, by urging the pusher member 634 axially in the distal direction relative to the handle 616 will also cause the needle cannula 628 to move with the pusher member 634. In the pre-deployed configuration shown, however, the safety tab 648 is releasably coupled (e.g., clipped or snapped over) the pusher member 634 and abuts the end plate 746 on one end and the proximal end 662 of the handle upper member 660 on the opposing end. Accordingly, the safety tab 648 prevents unintended axial movement of the pusher member 634 relative to the handle 616. It will be appreciated, however, that removal of the safety tab 648 from the pusher member 634 will allow the pusher member 634 and the needle cannula 628 to be advanced distally relative to the handle 616 and the outer tubular member 620.

As further shown in FIG. 9B, the lever 646 is pivotally connected to the lower portion 664 of the handle 616 at a pivot point 810, and itself includes an upper portion 816, a lower portion 820, and a resilient member 826 extending from the lower portion 820. In the illustrated embodiment, the upper portion 816 is disposed within the interior of the handle 616 and is shaped to engage the proximal portion 696 of the needle cannula 628. Additionally, the lower portion 820 partially extends from the handle lower portion 664, and the resilient member 826 bears against a wall 830 of the handle 616 interior. Thus, when the lower portion 820 of the lever 646 is urged into the handle lower portion 664, the upper portion 816, which is engaged with the proximal portion 696 of the needle cannula 628, will tend to urge the needle cannula 628 proximally relative to the handle 616. As will be appreciated, however, in the pre-deployed configuration shown, such proximal movement of the needle cannula 628 is prevented by the tab 748 of the pusher member 634, which is captured within the rear segment 676 of the lower slot 674 in the handle upper portion 660. The resilient member 826 operates to bias the lower portion 820 of the lever 646 away from the handle 616, thereby enhancing the tactile feel and control of the operation of the lever 646 by the clinician. In various embodiments, a spring or other biasing element can be utilized in lieu of or in addition to the resilient member 826, or alternatively, this biasing function can be eliminated altogether.

As can perhaps be best seen in FIG. 9C, the anchor member 650 is disposed within the needle cannula 628 proximate the open distal end 704, with the distal end 744 of the pusher member 634 abutting the anchor member 650. As further shown, the adjustable suture assembly 654 extends outward of the delivery tool 600 through the slots 692 and 736 in the outer tubular member 620 and the needle cannula 628, respectively. As shown in FIG. 9B, the toggle line 766 extends external to the delivery tool 600 and is connected to the flange 718 on the needle cannula proximal portion 696. In the pre-deployed configuration shown, the toggle line 766 operates, at least in part, to prevent the anchor member 650 from unintentionally being ejected from the delivery tool 600.

Additionally, the tension line 760 extends external to the delivery tool 600 and is connected to the safety tab 648. As further shown in FIGS. 9A and 9B, the delivery tool 600 also includes a suture management element 836, which in the illustrated embodiment is an elastic band or sleeve disposed about the outer tubular member 620 near its distal end 624. The suture management element 836 operates to releasably retain portions of the suture assembly 654 against the outer tubular member 620 prior to and during deployment of the implant 110, similar or identical to the elastic band (473) described in co-pending and commonly assigned U.S. application Ser. No. 12/553,583, which is incorporated herein by reference.

Figure 14A:
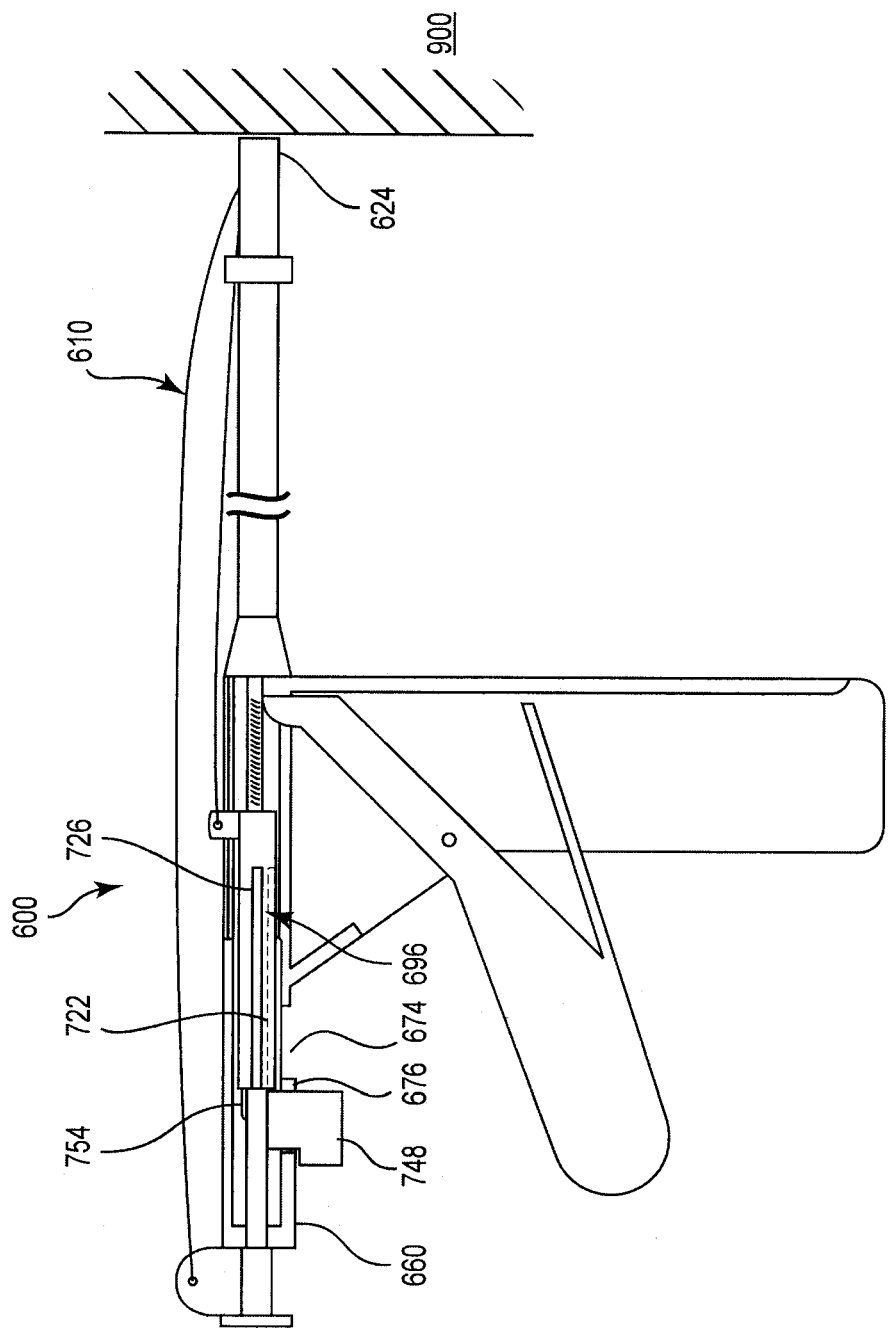
FIGS. 14A-14E are partial cut-away elevation views of the implant delivery tool of FIGS. 9A-9C during use to deploy the implant partially within a vertebra of a patient.

FIGS. 14A-14E are partial cut-away elevation views of the implant delivery tool 600 during use to deploy the implant 610 partially within a vertebral body 900 of a patient. As shown in FIG. 14A, the delivery tool 600 is initially positioned with the distal end 624 of the outer tubular member 620 abutting the surface of the vertebral body 900 at the desired implantation location for the anchor member 650 (not shown in FIG. 14A). In this configuration, as explained above, the tab 748 of the pusher member 634 is positioned in the rear segment 676 of the lower slot 674 in the handle upper portion 660, and the tab 748 and the projection 754 of the pusher member 634 are not radially aligned with the slots 722, 726 of the needle cannula proximal portion 696, but rather, abut and bear against the proximal portion 696.

Figure 14B:
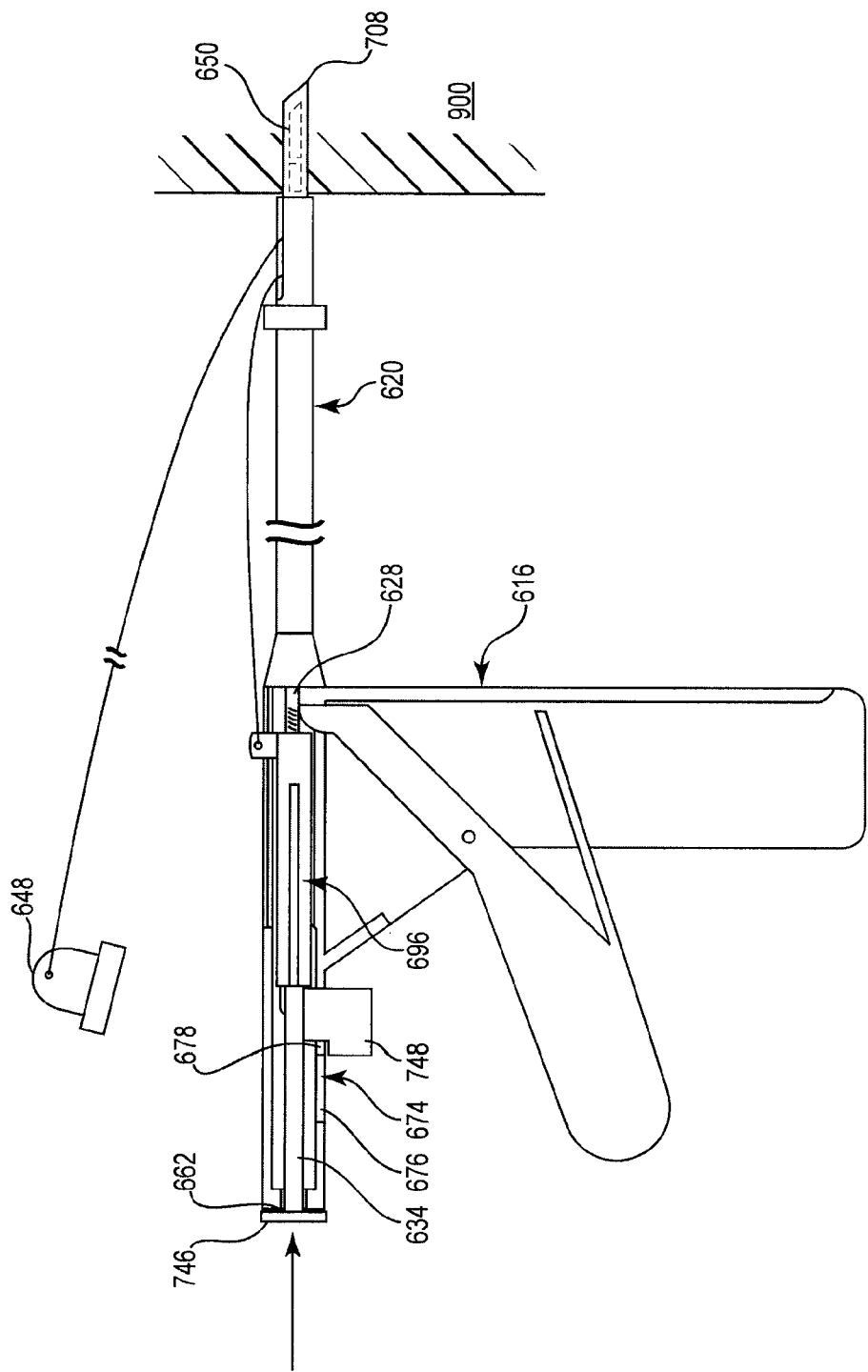

Then, as shown in FIG. 14B, the safety tab 648 is removed from the pusher member 634 and set aside, and the needle cannula 628 (with the anchor member 650 disposed therein) and the pusher member 634 are advanced distally so as to drive the sharpened distal tip 708 of the needle cannula into the vertebral body 900. In various embodiments, for example, a mallet can be used to tap against the end plate 746 of the pusher member 634. Because the tab 748 and the projection 754 of the pusher member 634 abut and bear against the proximal portion 696 of the needle cannula 628, distal movement of the pusher member 634 also moves the needle cannula 628 distally relative to the handle 616 and the outer tubular member 620 a desired distance into the vertebral body 900.

The pusher member 634 and other elements of the delivery tool 600 are, in various embodiments, dimensioned to provide a sufficient depth of penetration of the needle cannula 628 into the bone to facilitate deployment of the anchor member 650 and also encourage strong engagement with the bone. For example, in one embodiment, the length of the safety tab 648 is selected to correspond to the desired depth of penetration into the vertebral body 900, such that the needle cannula 628 will automatically be inserted the desired depth when the end plate 746 abuts the proximal end 662 of the handle upper portion 660, as shown in FIG. 14B.

Figure 14C:
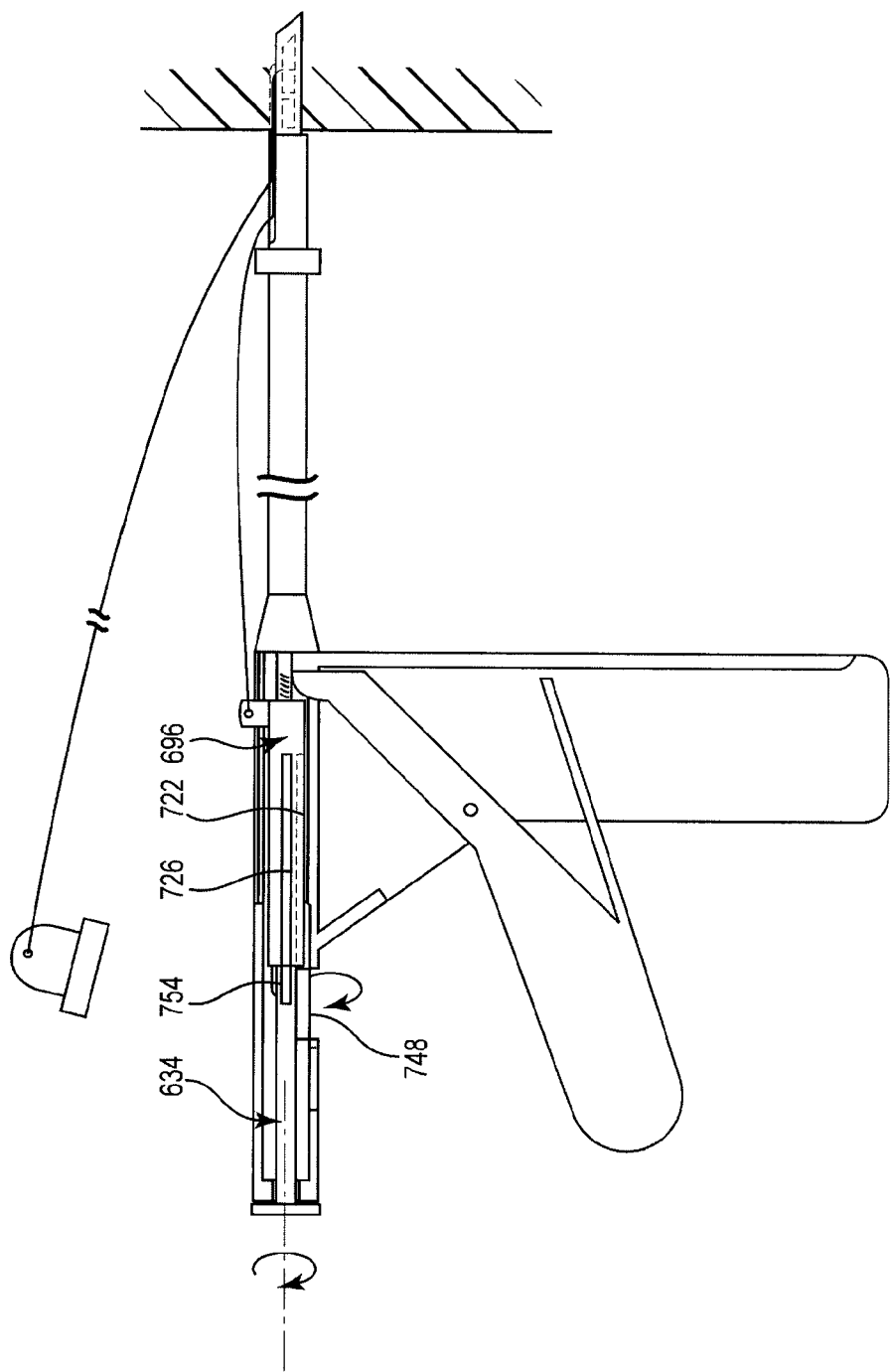

With the needle cannula 628 and the pusher member 634 fully advanced distally relative to the handle 616 and the outer tubular member 620, the tab 748 is positioned in the forward segment 678 of the lower slot 674 in the upper handle portion 660. As explained above, the width Wf of the forward segment 678 is greater than the width Wr of the rear segment 676. As shown in FIG. 14C, the tab 748 (and consequently, the pusher member 634) is then rotated to align the tab 748 and the projection 754 with the slots 722, 726 in the proximal portion 696 of the needle cannula 628. Rotation of the tab 748 also aligns the tab 748 with the recess 688 in the forward segment 678 of the lower slot 674 (see FIG. 10C). When so aligned, slight proximal movement of the pusher member 634 causes the tab 748 to be received in the recess 688, so that subsequent rotation of the tab 748 and the pusher member 634 are prevented by the projection 686. Additionally, the shoulder 682 formed in the lower slot prevents the pusher member 634 from being displaced proximally when in this configuration.

Figure 14D:
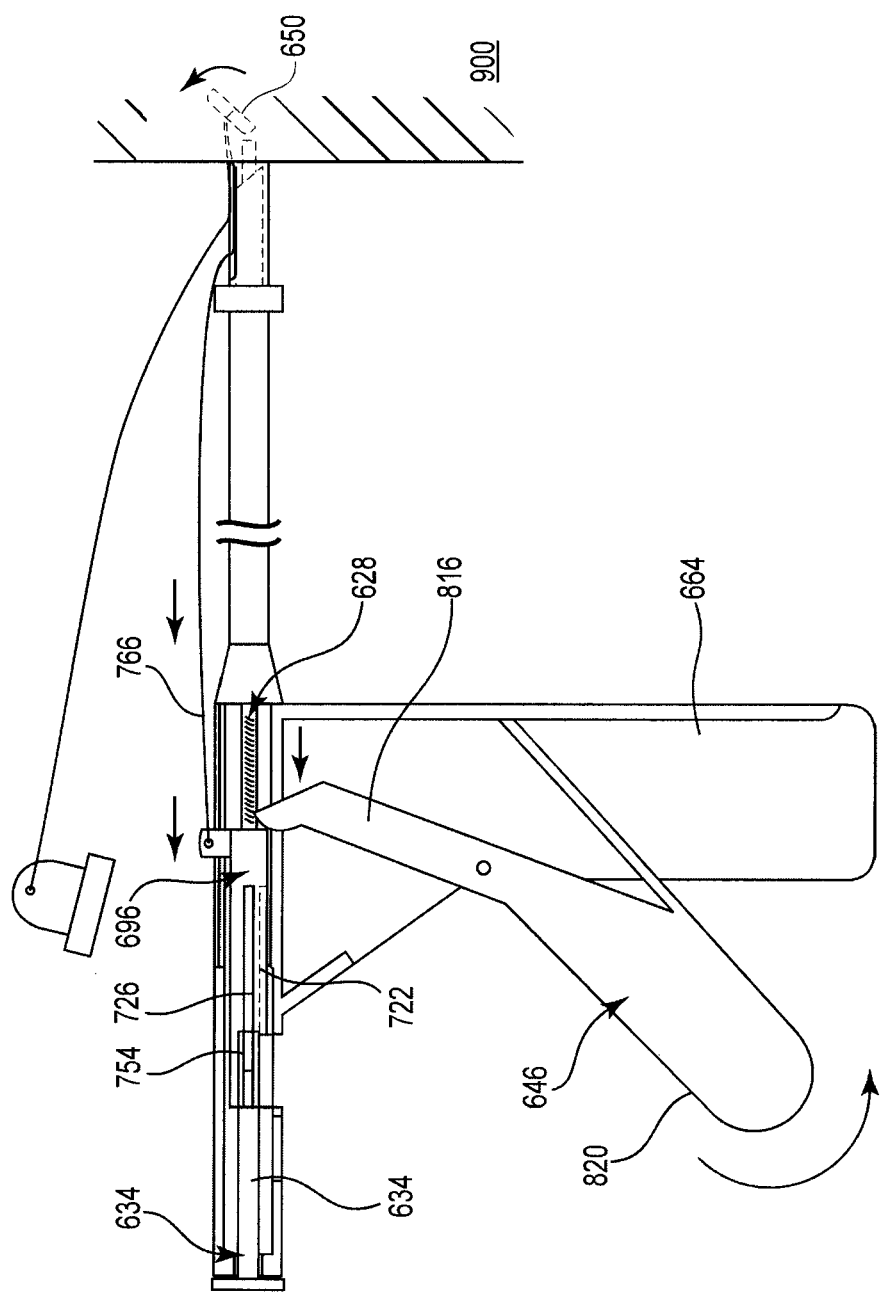

With the tab 748 and the projection 754 now aligned with the slots 722, 726 in the proximal portion 696 of the needle cannula 628, as shown in FIG. 14D, the lower portion 820 of the lever 646 is then urged into the handle lower portion 664, thereby pivoting the lever 646 and causing the upper portion 816 of the lever 646 to engage the proximal portion 696 of the needle cannula 628 and urge the needle cannula 628 proximally relative to the handle 616. As such, the needle cannula 628 is retracted relative to the pusher member 634, which remains stationary and prevents the anchor member 650 from being retracted with the needle cannula 628. Accordingly, as shown, the anchor member 650 is ejected from the needle cannula 628 and into the vertebral body 900.

Figure 14E:
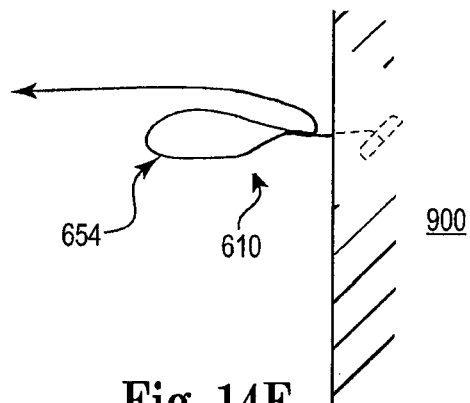

As further shown, retraction of the needle cannula 628 applies a tensile force to the toggle line 766 attached to the flange 718 of the needle cannula proximal portion 696. This in turn tends to cause the anchor member 650 to rotate as it is ejected from the needle cannula 628, which encourages positive engagement of the anchor member 650 with the vertebral body 900. In one embodiment, the toggle line 766 is configured to break at a selected location as the needle cannula 628 is retracted and the tension in the toggle line 766 exceeds a predetermined value, thereby allowing the toggle line 766 to be removed without requiring a separate cutting step. As shown in FIG. 14E, the delivery tool 600 can then be removed, leaving the implant 610 in place with the adjustable suture assembly 654 exposed for use in completing the anular repair procedure.

Figure 15A:
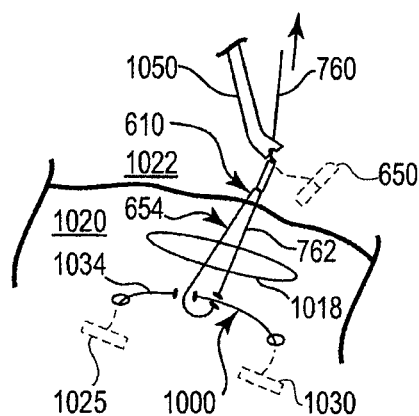
FIG. 15A-15F are schematic illustrations showing the implant of FIGS. 9A-9C being deployed in conjunction with a second implant to re-approximate an aperture or defect in a patient's intervertebral disc according to one embodiment of the present invention.
Figure 15B:
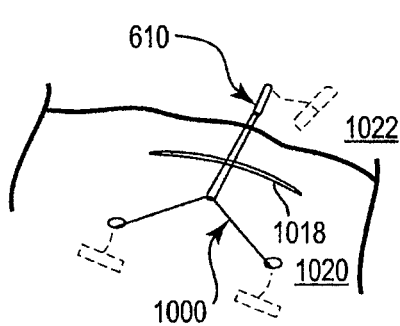
Figure 15C:
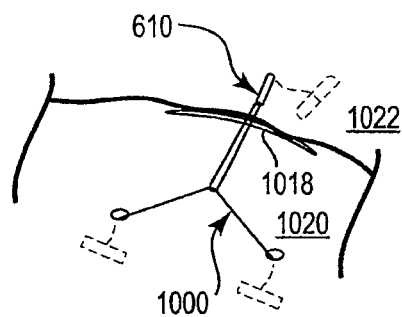

FIG. 15A-15C are schematic illustrations showing the implant 610 deployed in conjunction with a second implant 1000 to re-approximate an aperture or defect 1018 in a patient's intervertebral disc 1020 adjacent a vertebral body 1022 according to one embodiment of the present invention. In the illustrated embodiment, the implant 1000 includes a pair of tissue anchors 1025, 1030 connected by an adjustable connecting element 1034. The implant 1000 can, in various embodiments, be substantially similar or identical to the implants 25, 400 described above, as well as any of the dual anchor fixation devices disclosed, for example, in co-pending and commonly assigned U.S. patent application Ser. Nos. 12/251,295 and 12/553,583, and commonly assigned U.S. Provisional Application 61/293,939 the entire disclosures of which are incorporated herein by reference in their entireties. Accordingly, the implant 1000 is, in various embodiments, deployed using a delivery tool having a tubular member with a sharp tissue penetrating tip for penetrating the disc annulus, wherein the implant 1000 is received within the tubular member of the aforementioned delivery tool and is deployed in the annulus fibrosus as disclosed in any of the foregoing U.S. patent applications.

As shown in FIG. 15A, in one embodiment, the implant 610 is implanted with the anchor member 650 deployed in the patient's vertebral body 1022 such that the suture assembly 654 lays across the anular aperture 1018. The implant 1000 is implanted at a location such that the aperture 1018 is located between the implant 1000 and the vertebral body 1022. As shown, the tissue anchor 1025 is implanted in the patient's intervertebral disc 1020 in such a way that the connecting element 1034 extends out of the disc 1020 and through the loop 762 in the implant 610. As further shown, the tissue anchor 1030 is implanted at a second location in the disc 1020 using a delivery tool such as the delivery tools 20, 482 described above or any of the fixation delivery apparatuses disclosed in one of the above-mentioned U.S. patent applications, and is thereafter tightened using a tension guide or other technique. As further shown in FIG. 15A, a tension guide 1050 is used while tension is applied to the tension line 760 of the implant 610 (e.g., by pulling on the tab 748 attached to the free end 784 of the tension line 760) to cinch up the tension line 760 and reduce the dimensions of the loop 762. Accordingly, both the suture assembly 654 of the implant 610 and the connecting element 1034 of the implant 1000 are placed in tension and, by virtue of their implantation locations, urge the edges of the aperture 1018 together and toward the vertebral body 1022 to re-approximate the aperture 1018. FIG. 15B illustrates the implants 610, 1000 in their final implanted configurations, with the aperture 518 at least partially, if not wholly, closed. The implants 610, 1000 and the associated delivery tools, e.g., the delivery tool 600 and the delivery tool used to deploy the implant 1000 such as disclosed in any of the above-mentioned U.S. patent applications, as well as the tension guide 1050, thus form an anular repair system.

FIG. 15C illustrates an alternative use of the system including the implants 610, 1000 in their deployed states to repair a defect 1018 in the annulus fibrosus of the patient's intervertebral disc 1020. In the illustrated embodiment of FIG. 15C, the defect 1018 is a rim lesion, i.e., a tear/delamination of the annulus fibrosus from the vertebral body 1022 at the insertion point of the annulus into the vertebral body 1022. As such, the defect 1018 is located directly adjacent to the vertebral body 1022, such that there is there is little or no annulus fibrosus tissue between the defect 1018 and the vertebral body 1022. As shown, the implants 610 and 1000 are used to force the edge of the annulus fibrosus of the intervertebral disc 1020 back into contact with the adjacent surface of the vertebral body 1022 so as to at least partially, if not wholly, close the defect 1018.

Figure 15D:
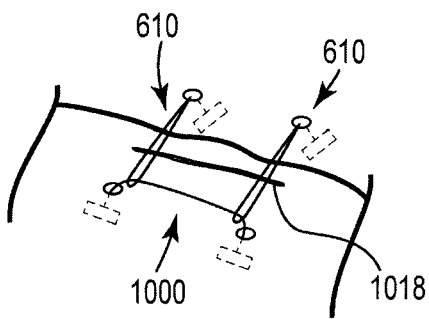
Figure 15E:
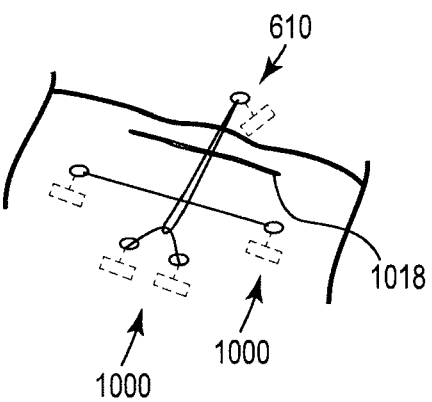
Figure 15F:
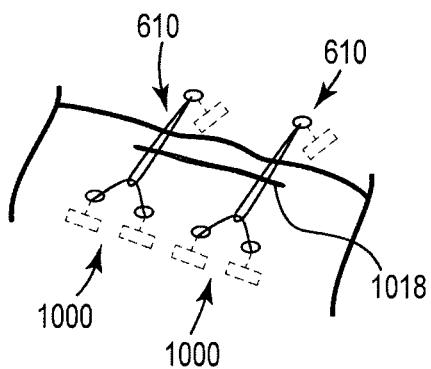

FIGS. 15D-15F illustrate alternative configurations utilizing one or more implants 610 and implants 1000 to repair the defect 1018 in the annulus fibrosus. As can be seen in FIGS. 15D-15F, any number of configurations of these implants can be employed to accomplish annulus repair, depending on the particular therapeutic needs of the patient.

Although in the figures above the anchor member 650 is illustrated and primarily described as being configured for deployment in the patient's vertebral body for repair of a defect in the adjacent annulus fibrosus, the implant 610, and the delivery tool 600, can also advantageously be used for other orthopedic applications. For example, the anchor member 650 can be readily deployed in soft tissue such as the annulus fibrosus itself using the delivery tool 600. In various embodiments, the anchor member 650 can advantageously be deployed in other soft tissues, and the delivery tool 600 can be used for deploying the anchor member 650 into such tissues. Additionally, the use of the implant 610 and the delivery tool 600 is not limited to use in intervertebral disc repair, but may also be utilized to repair defects in, for example, the joints in the hand or foot, knee, or shoulder.

Figure 16A:
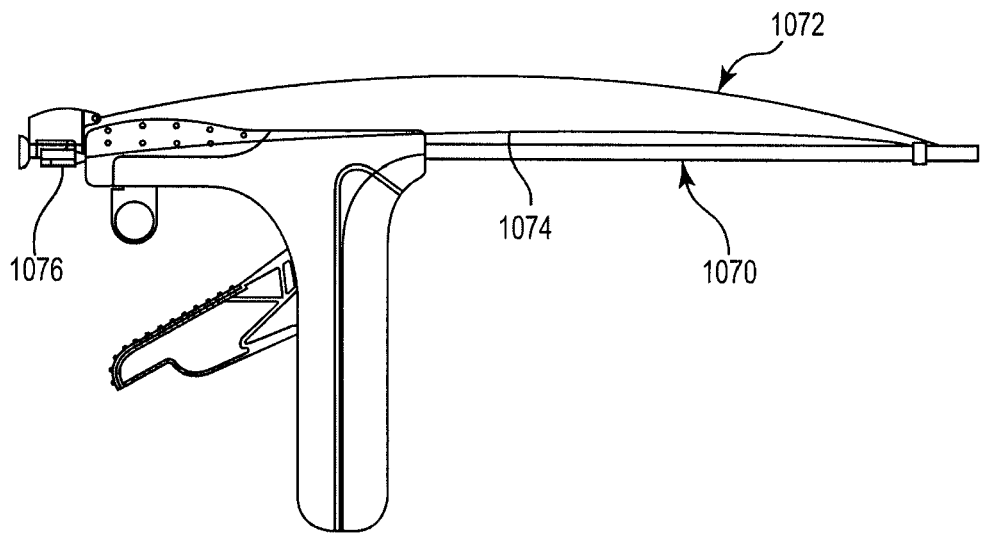
FIGS. 16A-16B are elevation views of an alternative implant delivery tool with an implant coupled thereto according to another embodiment of the present invention.
Figure 16B:
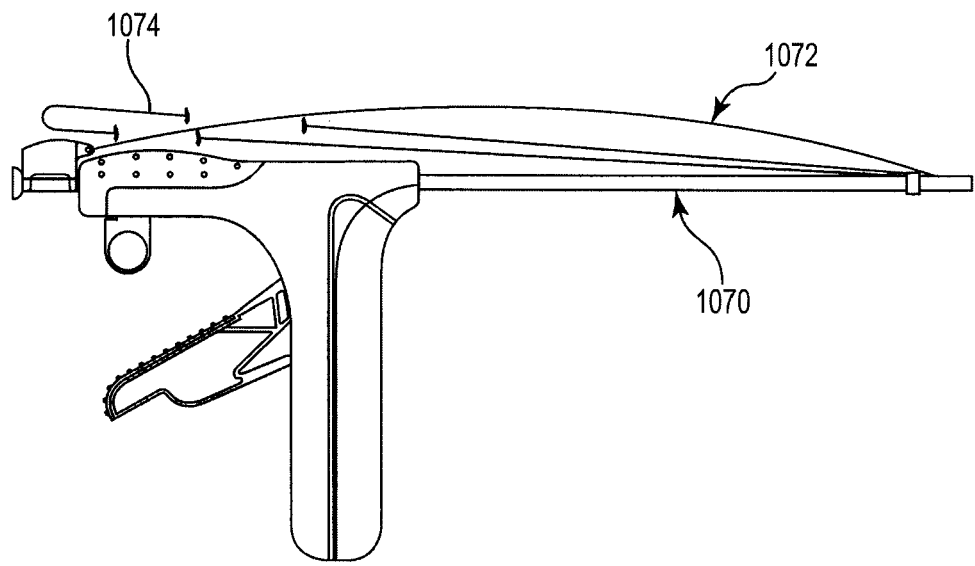

FIGS. 16A and 16B are plan views of an alternative embodiment of an implant delivery tool 1070 with an implant 1072 coupled thereto according to another embodiment of the present invention. The implant delivery tool 1070 and the implant 1072 are, except as noted below, substantially the same or identical in structure and function to the implant delivery tool 600 and the implant 610, respectively, described above, and thus need not be described in detail again here. The implant 1072 differs from the implant 600 in that the implant 1072 includes a toggle loop 1074 in lieu of the toggle line 766 of the implant 600. In the illustrated embodiment, the toggle loop 1074 is releasably retained against the implant delivery tool 1070 by a clip 1076 or other retaining element prior to deployment. In use, after deploying the anchor member (not shown) of the implant 1072 into bone or other tissue, the toggle loop 1074 is freed from the implant delivery tool 1070 and pulled manually by the physician to toggle the anchor member and confirm that the anchor member is positively engaged with the bone or other tissue. Any remaining length of the toggle line can then be cut away using a suture cutter or other cutting device.

FIGS. 17A-17D are elevation, detail perspective and partial cross-sectional views of the tension guide 1050 shown in FIG. 15A. As shown in FIGS. 17A-17D, the tension guide 1050 has a body 1090 having opposite first and second ends 1100, 1110 and a length therebetween. As further shown, the first end 1100 has a canted tip 1115 with a slot 1120 sized to slidingly receive a suture. The first end 1100 is thus in many respects similar or identical to the corresponding ends of conventional tension guides and/or knot pushers, and thus need not be described in greater detail here. In short, in use, a suture tightened is inserted into the slot 1120 with the canted tip 1115 bearing against the adjustable element (e.g., the locking element 788 of the tension line 760 described above, or alternatively, a knot such as a Roeder or Weston knot) to be tightened. Tension is applied to the suture while the tension guide resists movement of the locking element 788 or similar structure in the direction of the tensile force, so as to cinch up the suture. The foregoing is illustrated, for example, in FIG. 15A above in connection with tightening the suture assembly 654 of the implant 610.

Figure 17A:
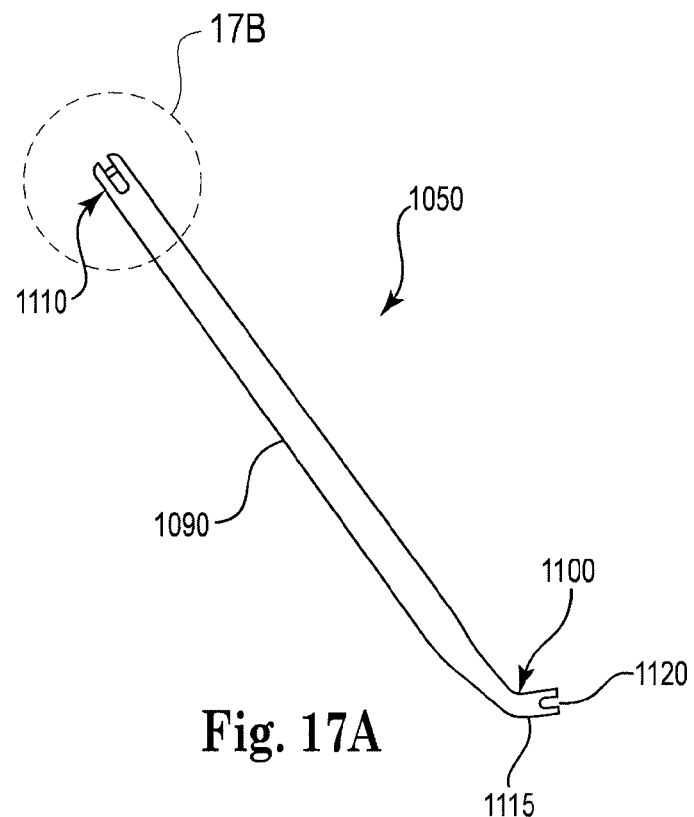
FIGS. 17A-17D are elevation, detail perspective and partial cross-sectional views of a tension guide for use in conjunction with the implants of FIGS. 5A-5B, 6A-6B, and 13 according to one embodiment of the present invention.
Figure 17B:
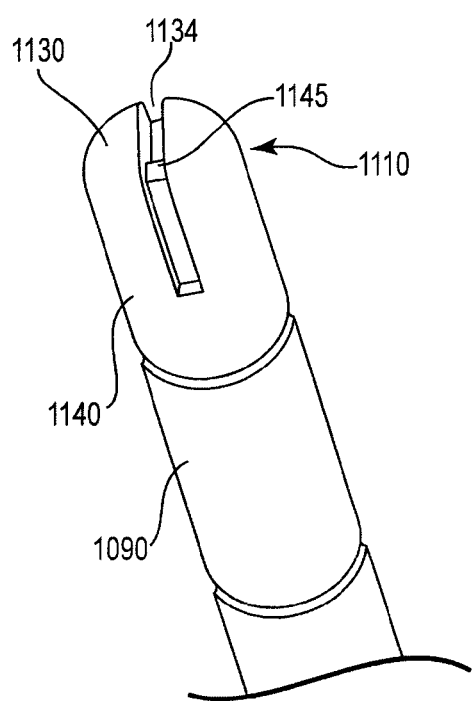

As shown in FIG. 17B, the second end 1110 includes a tip 1130 having a slot 1134 extending axially inward thereof. As further shown, within the slot 1134 is a blade 1140 having a cutting edge 1145 oriented toward the tip 1130. As shown, the blade 1140 is recessed inward from the periphery of the tip 1130, and the cutting edge 1145 is further axially recessed from the tip 1130. Thus, no portion of the blade 1140 extends outward of the body 1090 of the tension guide 1050. The slot 1134 is dimensioned, e.g., has a width and depth sufficient to freely receive any suture on which the tension guide 1050 is used. The blade 1140 is operable to cut away any excess suture length.

Figure 17C:
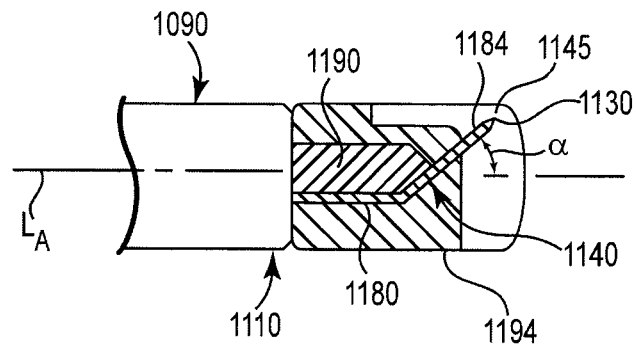

FIG. 17C is a partial cross-sectional elevation view of the second end 1110. As shown in FIG. 17C, in one embodiment, the blade 1140 includes a proximal segment 1180 and a distal segment 1184 terminating in the tip 1130. As further shown, the distal segment 1184 is angled relative to the proximal segment 1180 and the longitudinal axis $L_A$ of the tension guide 1050 in general. As further shown, the body 1090 includes an internal post 1190 to which the blade 1140 is secured. In various embodiments, the body 1090 further includes a slotted cap 1194 that is placed over the blade 1140 and the post 1190 and ultrasonically welded or otherwise secured in place to form the second end 1110 of the tension guide 1050. The cap 1194 operates to both shield the cutting edge 1145 of the blade 1140 as well as secure the blade 1140 to the body 1090.

Figure 17D:
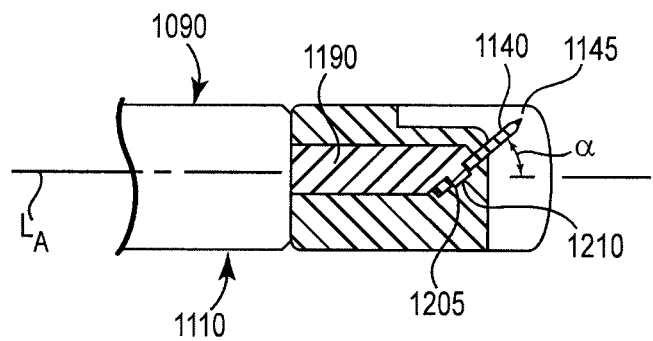

FIG. 17D is a partial cross-sectional elevation view of the second end 1110 of an alternative embodiment of the tension guide 1050 utilizing a different blade configuration than that shown in FIG. 17C. In the embodiment of FIG. 17D, the blade 1140 does not include a proximal segment. Rather, as shown in FIG. 17D, the blade 1140 extends only along an angled surface of the post 1190 and is mounted and secured to the post 1190. Additionally, in the embodiment of FIG. 17D, the blade 1140 includes a cutout 1205 sized to receive a tab 1210 on the post 1190 to facilitate mounting the blade 1140 to the post 1190.

In both FIGS. 17C and 17D, the portion of the blade 1140 terminating in the cutting edge 1145 is angled relative to the longitudinal axis of the tension guide 1050. In various embodiments, the angle α between the active portion of the blade 1140 and the longitudinal axis can be up to 90 degrees. In one embodiment, the angle α is about 45 degrees. The angle α is selected to allow the user to use a straight approach when cutting the suture (e.g., the body 1090 and the tension guide 1050 in general are generally aligned with the suture being cut). This straight approach is advantageously employed in procedures in which access is limited. Using the straight approach allows the user to position the suture in the slot 1134, and once positioned the user can gently pull the suture straight up and contact the cutting edge 1145 of the blade 1140, which severs the suture. The tension guide 1050 can also be used at any angle that allows the blade 1140 and the cutting edge 1145 to contact the suture. In various embodiments, the blade 1140 is not angled relative to the longitudinal axis of the tension guide 1050.

The cutting edge 1145 of the blade 1140 is not limited to any particular configuration or profile. In various embodiments, the cutting edge 1145 can have a single or double bevel, or a triple angled bevel. In various embodiments, the cutting edge 1145 can be either single sided or double sided. In various embodiments, the cutting edge 1145 can have a straight, concave or convex profile.

Thus, the tension guide 1050 advantageously provides a single tool that can be used by the clinician to both tighten a suture assembly (e.g., the suture assembly 654 of the implant 610) and cut away any excess suture material. Thus in use, the clinician uses the first end 1100 to tighten the suture assembly, and then inverts the tension guide 1050 and uses the second end 1110 and the blade 1140 to cut away any excess suture length. Because the cutting edge 1145 is recessed axially from the tip 1130, it is shielded to avoid unintentionally contacting tissue or portions of the suture assembly to be cut. The small diameter and low profile shape of the tension guide 1050 provide excellent functionality and is well adapted for use within the relatively small diameter access cannulae typically used for anular repair procedures, and eliminates the need to use conventional cutting devices, e.g., surgical scissors and the like, which can be difficult to manipulate within such cannulae.

Although primarily described above in connection with an annulus fibrosus repair procedure, it is emphasized that the tension guide 1050 can advantageously be employed in any procedure, including both orthopedic and non-orthopedic procedures, to provide a safe, quick and efficient means to cut and remove excess suture material and, if applicable, tension the suture itself. For example, the tension guide 1050 is readily usable in orthopedic procedures such as meniscal repair procedures as well as shoulder and hip repair procedures. In one embodiment, the tension guide 1050 may be used to both tighten the connecting element 300 and remove excess suture material in the implant 25 when used to repair a tear or other defect in a meniscus of a patient's knee. Still other applications of the tension guide 1050, both in sports medicine or other orthopedic repair procedures, will be readily apparent to the skilled artisan based on the foregoing.

The tension guide 1050 can be made from a number of suitable biocompatible materials. In various embodiments, the body 1090 can be made from any of a variety of relatively rigid, biocompatible metal or polymeric materials. In various embodiments, the body 1090 is made from a polymer such as, without limitation, polypropylene, polyether etherketone (PEEK™), polyethylene, polyethylene teraphthalate (PET) and polyurethane, acrylic, polycarbonate, engineering plastics; and/or composites. In one embodiment, the body 1090 is made from PEEK™. The blade 1140 can be made from any of a variety of suitable metals or polymers. Suitable metals for use in the blade 1140 include, without limitation, stainless steel, nickel, titanium, and titanium and nickel alloys. In one embodiment, the blade 1140 is formed from stainless steel. In various embodiments, the blade 1140 includes a coating or other treatment to increase the hardness and wear resistance of the blade material. Suitable materials for the aforementioned coatings include, without limitation, titanium nitride, titanium carbide, titanium carbonitride, chromium nitride, diamond-like coatings, zirconium nitride, titanium aluminum nitride, and various non-stick materials such as polytetraflouroethylene (PTFE) and expanded PTFE. In other embodiments, the blade 1140 is not coated.

Figure 18A:
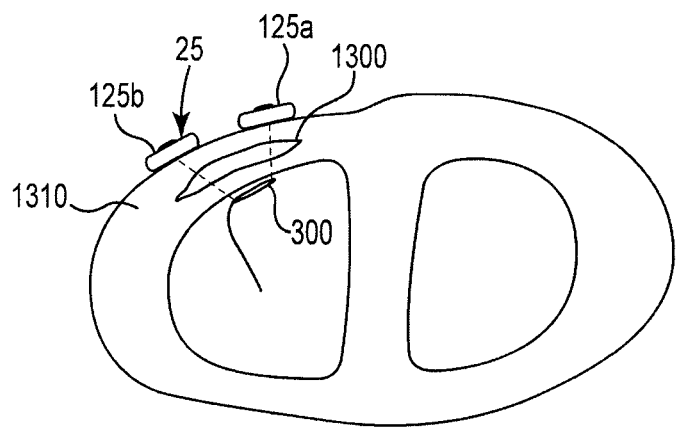
FIGS. 18A-18B are schematic illustrations showing the implant of FIG. 5A-5B or 6A-6B implanted to repair a defect or tear in a meniscus of the knee according to one embodiment of the present invention.
Figure 18B:
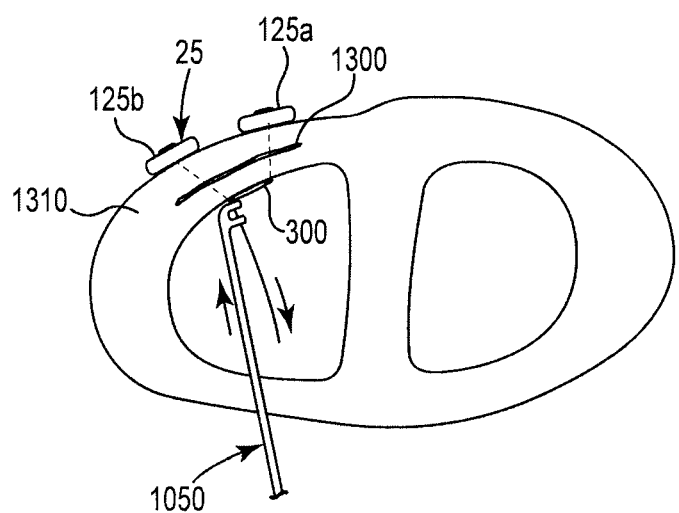

FIGS. 18A-18B are schematic illustrations of the implant 25 in use to repair a tear or other defect 1300 in a meniscus 1310 of a patient's knee according to yet another embodiment of the present invention. As shown in FIGS. 18A and 18B, in one embodiment, the tissue anchors 125a and 125b can be deployed on the outer surface of the meniscus 1310 with the connecting element 300 extending through the meniscus 1310 and bearing against the inner surface of the meniscus 1310 proximate the tear 1300. Thus, as shown in FIG. 18B, the connecting element 300 is irreversibly shortened using the tension guide 1050, and the meniscal tissue adjacent to the tear 1300 is urged together to effectuate the repair. Any excess suture material of the connecting element 300 is thereafter cut away using the tension guide 1050 as described above. Although FIGS. 18A and 18B illustrate the use of only a single implant 25, in various embodiments, additional implants 25 and/or implants 400 can be used to accomplish the meniscal repair. In still other embodiments, the implants 25, 400 can be used for other orthopedic repair procedures in the knee, shoulders, hips, and the like.

The materials used in the implants 610, 1000, 1072, and the delivery tools 600, 1010, 1070 can include any number of biocompatible materials having suitable mechanical properties. For example, materials from which to make the anchor member 650 and the tissue anchors 1025, 1030 can include, but are not limited to: metals, such as stainless steel, nickel, titanium alloy, and titanium; plastics, such as polytetrafluoroethylene (PTFE), polypropylene, polyether etherketone (PEEK™), polyethylene, polyethylene teraphthalate (PET) and polyurethane, acrylic, polycarbonate, engineering plastics; and/or composites. The adjustable suture assembly 654 and the connecting element 1034 can likewise be made of any suitable suture material. In various embodiments, the anchor member 650, the tissue anchors 1025, 1030 and/or the adjustable suture assembly 654 and the connecting element 1034 can be made of bio-resorbable materials. In various embodiments, the tension line 760, the toggle line 766 and the connecting segment 770 of the implant 610 are made wholly or partially of size 2-0 or 3-0 ultra high molecular weight polyethylene (UHMWPE) suture material, otherwise known as force fiber suture material. In one embodiment, the anchor member 650 is made from PEEK, the tension line 760 and the connecting segment 770 are made from size 2-0 UHMWPE suture material, and the toggle line 766 is made from size 3-0 UHMWPE suture material. In short, any suitable materials, whether now known or later developed, can be utilized to construct the implant 610 within the scope of the present invention.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:
1. A device for at least partially closing an aperture in an annulus fibrosus of an intervertebral disc of a patient, the device comprising:
an implant delivery tool including
a substantially rigid outer tube having a proximal section and a sharpened distal tip;
a body coupled to the proximal section of the outer tube;

a plunger assembly movable axially relative to the body and including a plunger member and a pusher tube coupled thereto and disposed within the outer tube; and an implant releasably coupled to the implant delivery tool including:

first and second tissue anchors serially disposed within the distal section of the outer tube; and a flexible connecting element coupling the first and second tissue anchors, the connecting element at least partially formed from a braided tubular suture material and including:

a distal segment of the braided suture material attached to the first tissue anchor;

an intermediate segment of the braided suture material extending proximally from the distal segment and including a locking element and an adjustable loop, wherein a portion of the intermediate segment extends internally within the braided suture material of the locking element, and wherein the second tissue anchor is slidably coupled to the braided suture material of the adjustable loop; and a proximal segment of the braided suture material extending proximally from the intermediate segment and releasably coupled to the implant delivery tool.

2. The device of claim 1 wherein the pusher tube is displaceable within the outer tube from a first position to a second position to eject the first tissue anchor from the outer tube.

3. The device of claim 2 wherein the pusher tube is further displaceable within the outer tube from the second position to a third position to eject the second tissue anchor from the outer tube.

4. The device of claim 1 wherein the implant delivery tool includes a releasable tab releasably coupled to the plunger assembly.

5. The device of claim 4 wherein the connecting element is partially disposed within the outer tube and the proximal segment of the flexible connecting element is coupled to the releasable tab of the implant delivery tool.

6. A device for at least partially closing an aperture in an annulus fibrosus of an intervertebral disc of a patient, the device comprising:

an implant delivery tool including:

a substantially rigid outer tube having a proximal section, an intermediate section, and a distal section terminating in a sharpened tissue-piercing distal tip having an open end, the intermediate section having a first length, wherein the proximal and distal sections are laterally offset from one another by the intermediate section;

a body coupled to the proximal section of the outer tube;

a plunger assembly including a plunger member slidably disposed within the body, and a pusher tube slidably disposed within the body and the outer tube and coupled to the plunger member, the pusher tube including a distal end and a flexible segment proximal to the distal end axially coincident with the intermediate portion of the outer tube, the flexible segment having a second length greater than the first length of the intermediate portion of the outer tube; and an implant releasably coupled to the implant delivery tool including a pair of tissue anchors serially disposed within the distal section of the outer tube, and an adjustable flexible connecting element connecting the tissue anchors, wherein the plunger assembly is operable by a user to selectively displace the pusher tube distally within the outer tube so as to serially eject the first tissue anchor and then the second tissue anchor from the open end of the outer tube.

7. The device of claim 6 wherein the pusher tube is displaceable within the outer tube from a first position to a second position to eject the first tissue anchor from the outer tube.

8. The device of claim 7 wherein the pusher tube is further displaceable within the outer tube from the second position to a third position to eject the second tissue anchor from the outer tube.

9. The device of claim 8 wherein the intermediate section of the outer tube is axially coincident with at least a portion of the flexible segment of the pusher tube when the pusher tube is in the first, the second and the third positions.

10. The device of claim 6 wherein the implant delivery tool includes a releasable tab coupled to the plunger assembly.

11. The device of claim 10 wherein a first portion of the connecting element is disposed within the outer tube and a second portion of the flexible connecting element is coupled to the releasable tab of the implant delivery tool.

12. The device of claim 6 wherein the flexible connecting element has an adjustable length so as to allow separation between the tissue anchors to be reduced after deployment.

13. The device of claim 12 wherein the flexible connecting element is a knotless suture arrangement including a locking element substantially preventing elongation of the flexible connecting element between the tissue anchors after deployment.

14. The device of claim 6 wherein the flexible segment of the pusher tube includes a series of slots extending circumferentially about the pusher tube in a helical pattern, the slots imparting lateral flexibility to the flexible segment.

15. The device of claim 14 wherein the slots have an undulating shape.

16. The device of claim 6 wherein the flexible segment of the pusher tube is heat treated to impart lateral flexibility to the flexible segment.

17. The device of claim 6 wherein the flexible segment of the pusher tube is in the form of a helical spring.

18. The device of claim 6 wherein the proximal and distal sections of the outer tube are substantially parallel to one another.

19. The device of claim 6 wherein the intermediate section of the outer tube has a first curved portion extending from the proximal section and a second curved portion extending proximally from the distal section having an opposite curvature to that of the first curved portion.

20. A device for at least partially closing an aperture in an annulus fibrosus of an intervertebral disc of a patient, the device comprising:

an implant delivery tool including a substantially rigid outer tube having a proximal section, a distal section, and an intermediate section having a nonlinear shape laterally offsetting the proximal and distal sections from one another;

a body coupled to the proximal section of the outer tube;

a plunger assembly movable axially relative to the body and including a plunger member and a pusher tube coupled thereto and disposed within the outer tube, the pusher tube having a substantially rigid proximal segment, a substantially rigid distal segment including a distal end, and a flexible segment between the proximal and distal segments, wherein the pusher tube is slidably displaceable within the outer tube to assume a plurality of positions, and wherein the flexible segment is configured to conform to the nonlinear shape of the intermediate section of the outer tube in each of the plurality of positions of the pusher tube; and an implant releasably coupled to the implant delivery tool including a pair of tissue anchors serially disposed within the distal section of the outer tube, and an adjustable flexible connecting element connecting the tissue anchors.

21. The device of claim 20 wherein the flexible segment of the pusher tube is dimensioned such that the intermediate section of the outer tube is axially coincident with at least a portion of the flexible segment in each of the plurality of positions of the pusher tube.

22. The device of claim 21 wherein the proximal and distal sections of the outer tube are substantially parallel to one another.

23. The device of claim 21 wherein the adjustable flexible connecting element is a knotless suture arrangement including a locking element substantially preventing elongation of the flexible connecting element between the tissue anchors after deployment.

24. The device of claim 21 wherein the flexible segment of the pusher tube includes a series of slots extending circumferentially about the pusher tube in a helical pattern, the slots imparting lateral flexibility to the flexible segment.

25. A system for at least partially closing an aperture in an annulus fibrosus of an intervertebral disc of a patient, the system comprising:

first and second repair devices each including:
an implant delivery tool including
a substantially rigid outer tube having a proximal section and a distal section terminating in a sharpened distal tip;
a body coupled to the proximal section of the outer tube;
a plunger assembly movable axially relative to the body and including a pusher tube disposed within the outer tube, wherein the pusher tube is slidably displaceable within the outer tube to assume a plurality of positions; and an implant releasably coupled to the implant delivery tool including:
first and second tissue anchors serially disposed within the distal section of the outer tube; and
a flexible connecting element coupling the first and second tissue anchors, the connecting element at least partially formed from a braided tubular suture material and including:
a distal segment of the braided suture material attached to the first tissue anchor;
an intermediate segment of the braided suture material extending proximally from the distal segment and including a locking element and an adjustable loop, wherein a portion of the intermediate segment extends internally within the braided suture material of the locking element, and wherein the second tissue anchor is slidably coupled to the braided suture material of the adjustable loop; and
a proximal segment of the braided suture material extending proximally from the intermediate segment and releasably coupled to the implant delivery tool.

\* \* \* \* \*